United States Patent
Friedman et al.

(10) Patent No.: US 11,154,692 B2
(45) Date of Patent: Oct. 26, 2021

(54) INTRALUMINAL DEVICE WITH LOOPED CORE WIRE

(71) Applicant: RAPID MEDICAL LTD., Yokneam (IL)

(72) Inventors: Aharon Friedman, Haifa (IL); Matan Gedulter, Givat Ela (IL); Ronen Eckhouse, Shimshit (IL); Moshe Miller, Jerusalem (IL)

(73) Assignee: RAPID MEDICAL LTD., Yokneam (IL)

( * ) Notice: Subject to any disclaimer, the term of this patent is extended or adjusted under 35 U.S.C. 154(b) by 0 days.

(21) Appl. No.: 16/668,248

(22) Filed: Oct. 30, 2019

(65) Prior Publication Data
US 2021/0128877 A1 May 6, 2021

(51) Int. Cl.
*A61M 25/01* (2006.01)
*A61M 25/09* (2006.01)
(Continued)

(52) U.S. Cl.
CPC .. *A61M 25/0147* (2013.01); *A61M 25/09016* (2013.01); *A61M 25/09041* (2013.01);
(Continued)

(58) Field of Classification Search
CPC ........ A61M 25/0147; A61M 2025/015; A61M 2025/09066; A61M 2025/09083;
(Continued)

(56) References Cited

U.S. PATENT DOCUMENTS 3,521,620 A * 7/1970 Cook .............. A61M 25/09033
600/585
4,815,478 A 3/1989 Buchbinder et al.
(Continued)

FOREIGN PATENT DOCUMENTS

WO WO 2018/060776 A2 4/2018
WO WO 2019/116102 A2 6/2019

OTHER PUBLICATIONS

International Search Report and Written Opinion of the International Searching Authority dated Jul. 10, 2018, in International Application No. PCT/IB2017/001663 (10 pages).
(Continued)

*Primary Examiner* — Nathan R Price
*Assistant Examiner* — Courtney B Fredrickson
(74) *Attorney, Agent, or Firm* — Finnegan, Henderson, Farabow, Garrett & Dunner, LLP

(57) ABSTRACT

Intraluminal and endovascular devices and methods of manufacturing intraluminal and endovascular devices may be provided. In one implementation, an intraluminal device may include a sheath having a flexible distal bending segment and a core wire arranged within the sheath. The core wire may include a distal end portion doubled back in a loop within the sheath such that the distal tip of the core wire is situated proximally from the loop. The intraluminal device may also include a movement restrictor within the sheath that is configured to limit axial movement of the distal tip of the core wire. Limiting the axial movement of the core wire distal tip may cause the loop of the core wire to buckle, resulting in a bend in the distal bending segment of the sheath, when a force is exerted on the core wire.

21 Claims, 13 Drawing Sheets

(51) Int. Cl.
  *A61B 17/12* (2006.01)
  *A61B 17/00* (2006.01)
(52) U.S. Cl.
  CPC ..... *A61B 17/00234* (2013.01); *A61B 17/1214* (2013.01); *A61B 2017/003* (2013.01); *A61M 2025/09066* (2013.01)
(58) Field of Classification Search
  CPC ...... A61M 25/09025; A61M 25/09041; A61B 2017/003
  See application file for complete search history.

(56) References Cited

U.S. PATENT DOCUMENTS

| | | | |
|---|---|---|---|
| 4,827,941 A | | 5/1989 | Taylor et al. |
| 4,940,062 A | * | 7/1990 | Hampton ........ A61M 25/09033 600/434 |
| 5,318,529 A | | 6/1994 | Kontos |
| 5,484,409 A | | 1/1996 | Atkinson et al. |
| 7,182,735 B2 | * | 2/2007 | Shireman .............. A61M 25/09 600/585 |
| 2003/0097128 A1 | * | 5/2003 | Hayzelden ......... A61B 18/1492 606/41 |
| 2003/0181827 A1 | | 9/2003 | Hojeibane et al. |
| 2004/0193205 A1 | * | 9/2004 | Burgermeister .. A61M 25/0152 606/194 |
| 2006/0200047 A1 | | 9/2006 | Galdonik et al. |
| 2009/0192495 A1 | * | 7/2009 | Ostrovsky ......... A61M 25/0009 604/528 |
| 2010/0004722 A1 | | 1/2010 | Täubert et al. |
| 2010/0249773 A1 | | 9/2010 | Clark et al. |
| 2010/0305475 A1 | | 12/2010 | Hinchliffe et al. |
| 2014/0343457 A1 | | 11/2014 | Shekalim et al. |
| 2014/0350568 A1 | | 11/2014 | Shekalim et al. |
| 2017/0209671 A1 | | 7/2017 | Ring |
| 2019/0240457 A1 | | 8/2019 | Sudin et al. |

OTHER PUBLICATIONS

International Search Report and Written Opinion of the International Searching Authority dated May 31, 2019, in International Application No. PCT/IB2018/001571 (6 pages).
U.S. Appl. No. 16/668,427; Rotationally Torquable Endovascular Device With Variable Flexibility Tip; Aharon Friedman et al; filed Oct. 30, 2019.

* cited by examiner

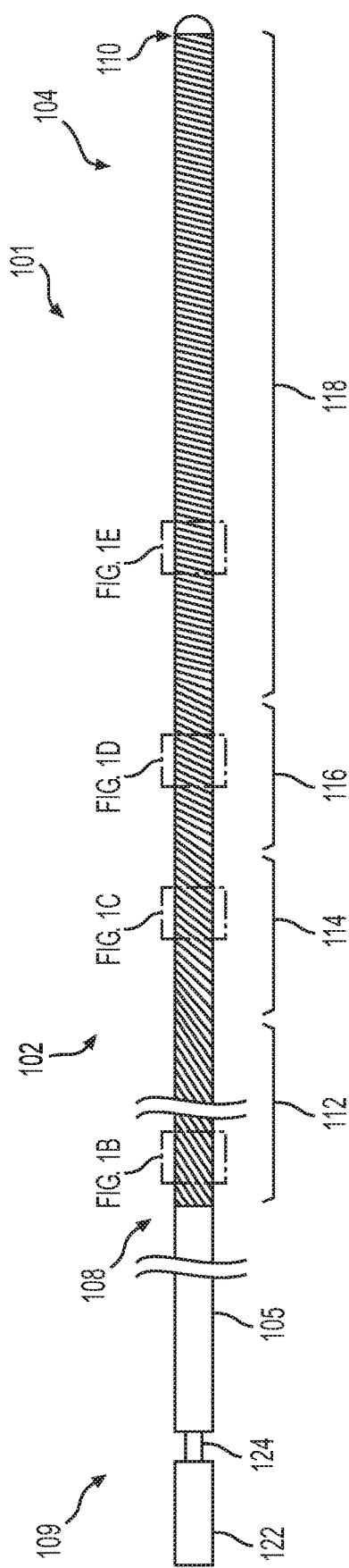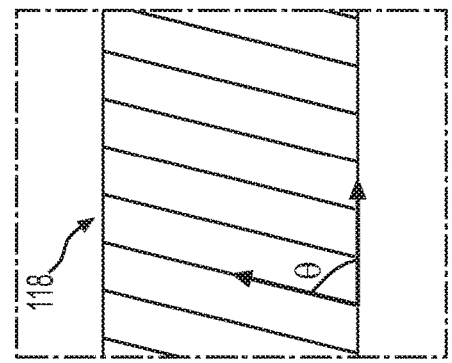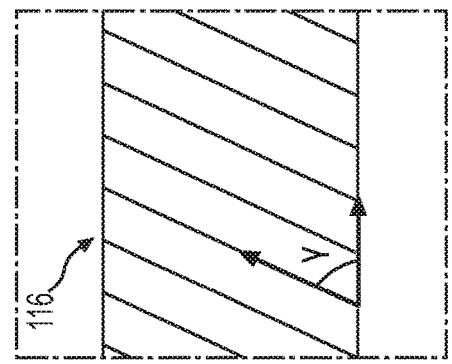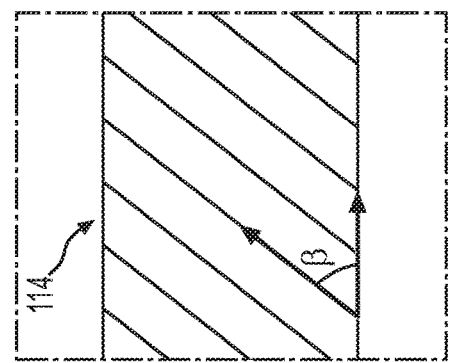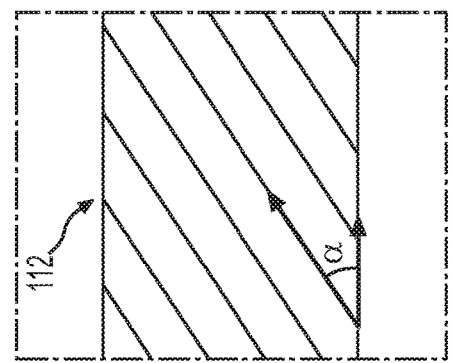

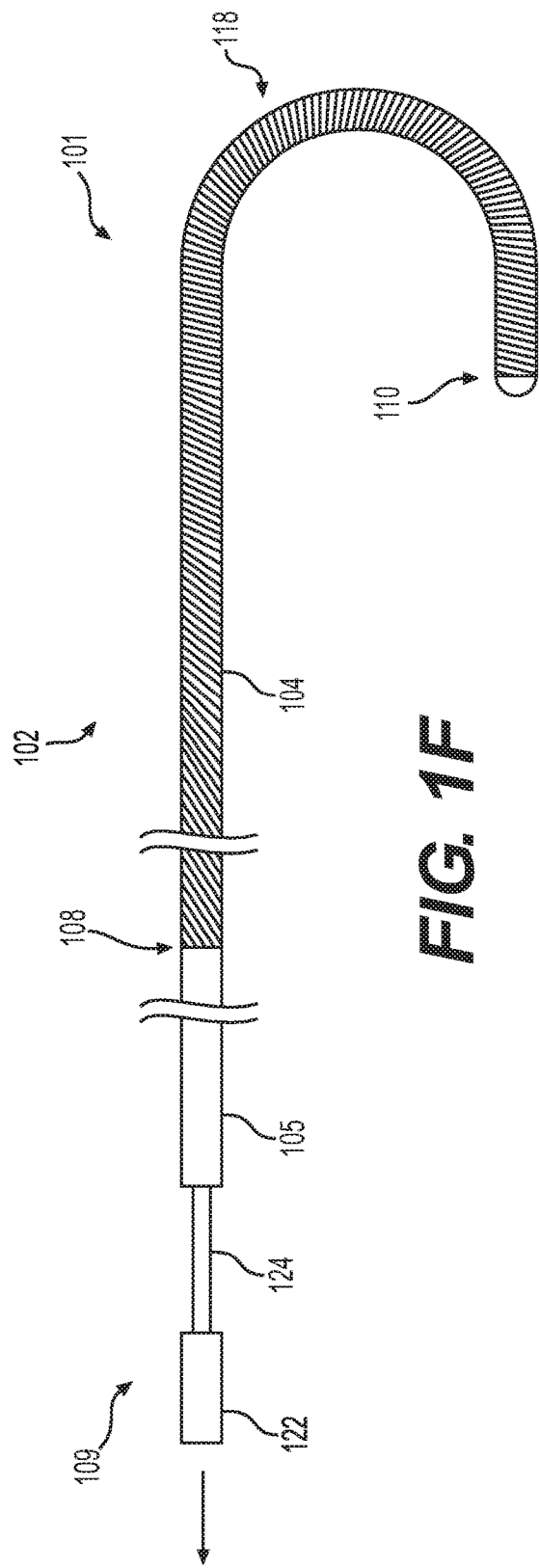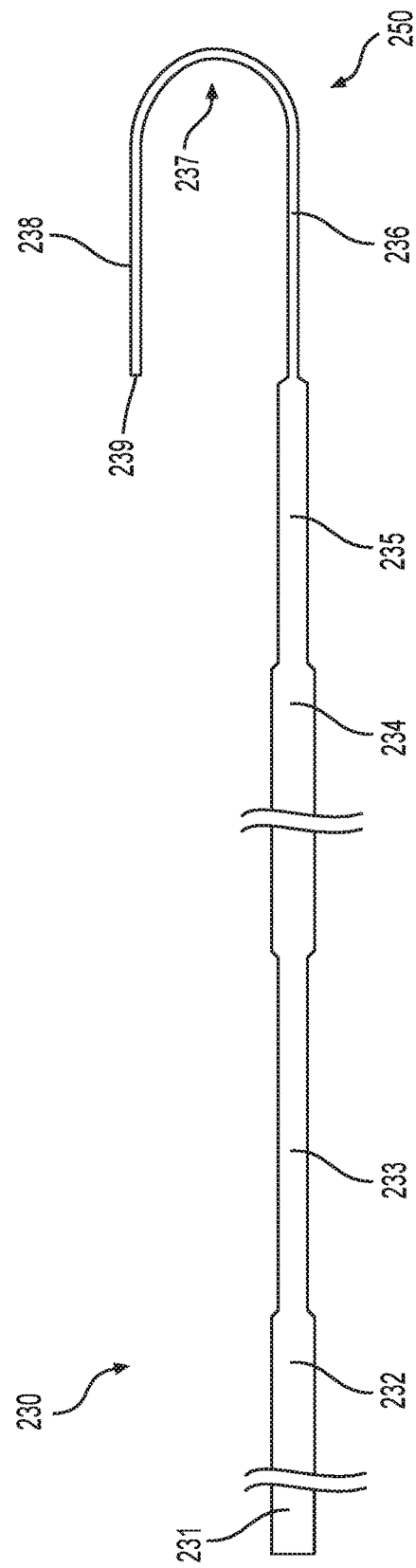

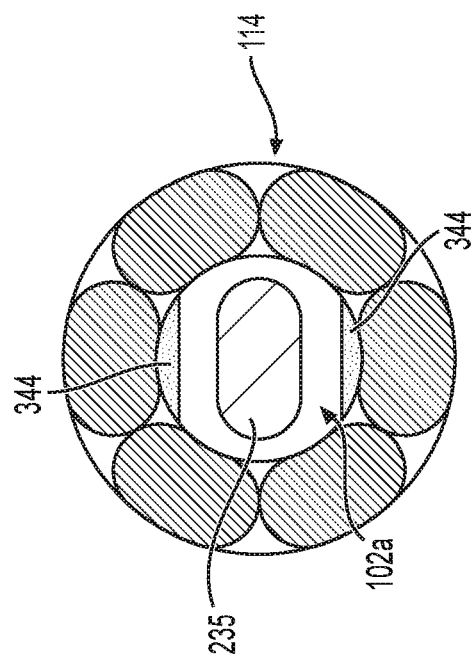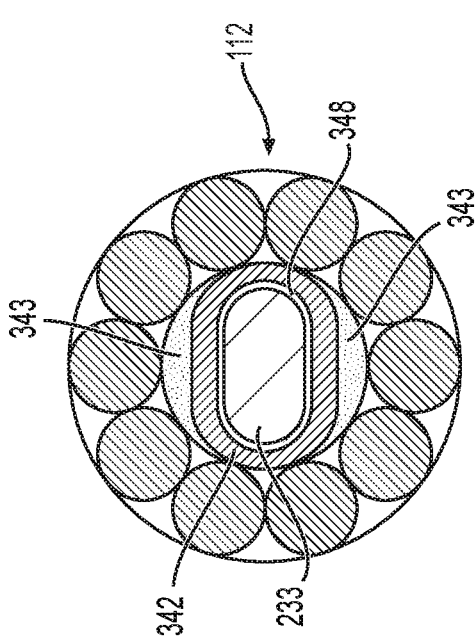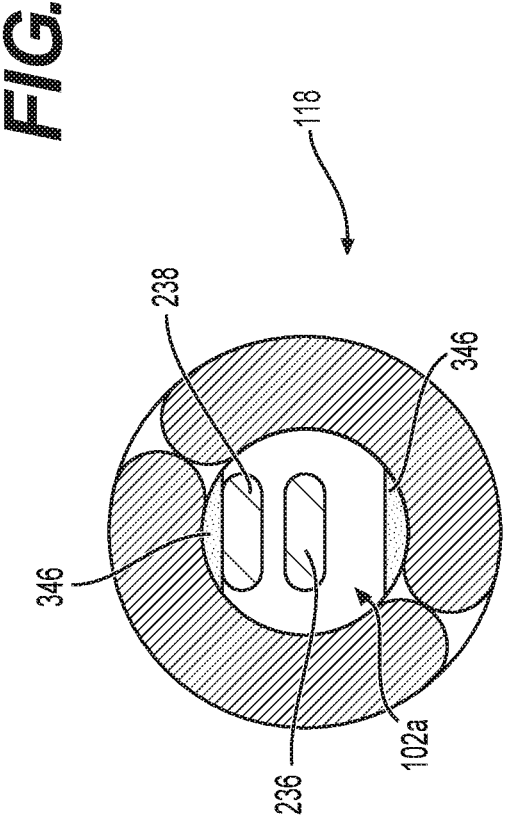

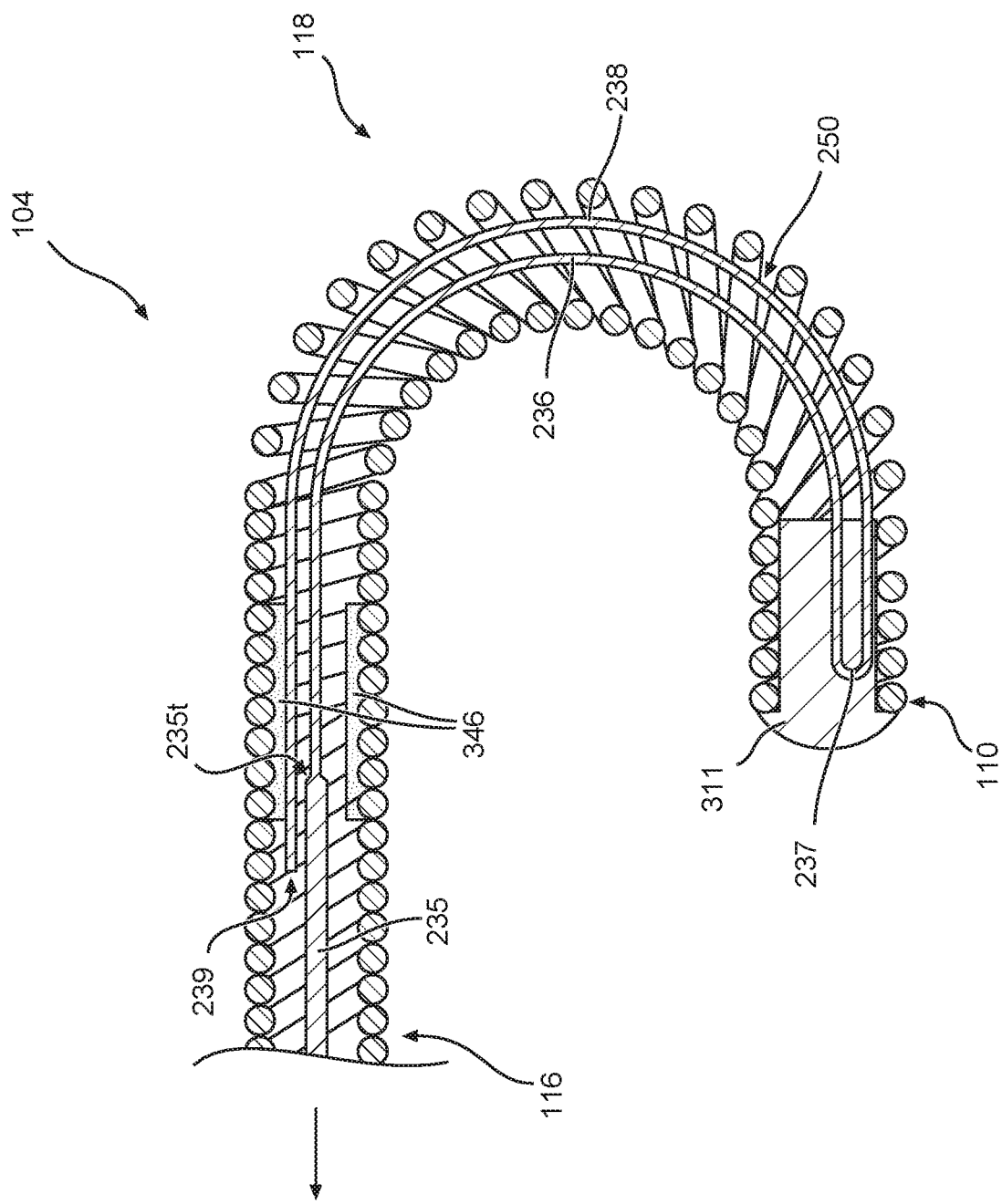

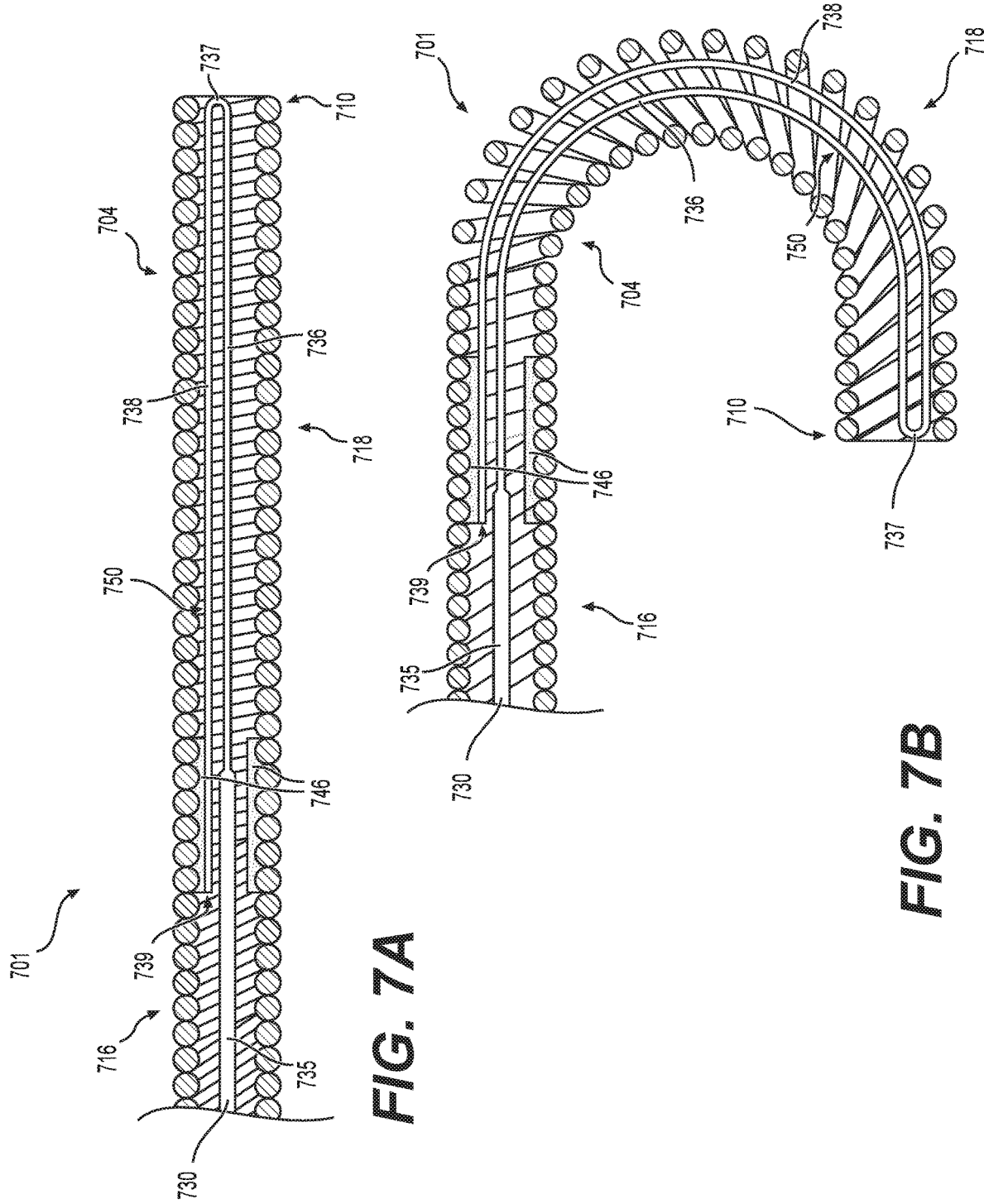

INTRALUMINAL DEVICE WITH LOOPED CORE WIRE

TECHNICAL FIELD

This disclosure relates to intravascular and intraluminal medical devices and systems having at least one looped core wire configured to improve steering of the device. The disclosure also relates to methods of manufacturing intravascular and intraluminal medical devices and systems.

BACKGROUND

Intravascular and intraluminal medical devices, such as guide wires and microcatheters, must be advanced through the body until the device reaches the desired treatment site. To pass through tortuous anatomy, the device may include a steering mechanism such as a pull wire, which may be configured to bend or deflect the distal tip of the device. The pull wire may be secured to a user actuation segment, such as a handle at the proximal end of the guide wire, which may be controlled by a user to steer the device. However, many devices have poor steerability, either requiring a large application of force by the user to affect a small bend in the device or producing inconsistent bending each time the pull wire is actuated. As a result, it is often difficult to steer the device through the anatomy, especially when the anatomy is small and tortuous.

Thus, there remains a need for intraluminal devices providing improved and consistent steering, while also exhibiting a sufficiently pliable distal tip in order to avoid potential complications as the device is delivered to a treatment site.

SUMMARY

Embodiments of the present disclosure may include an intraluminal device having a flexible, elongated sheath. The sheath may include a proximal portion and a distal portion, the distal portion of the sheath terminating in a distal end of the sheath. The distal portion of the sheath may include a distal bending segment and a proximal support segment situated proximally from the distal bending segment, the distal bending segment being configured for greater flexibility than the proximal support segment. The intraluminal device may also include an elongated core wire extending between a proximal tip of the core wire and a distal tip of the core wire. The core wire may be situated at least partially within the sheath. The core wire may include a distal end portion doubled back in a loop within the sheath such that at least a portion of the core wire may be situated proximally from the loop of the core wire. The intraluminal device may also include a movement restrictor situated at least partially within the sheath. The movement restrictor may be configured to limit axial movement of the distal tip of the core wire in at least one axial direction. The movement restrictor may also be configured to permit the loop of the core wire to buckle, resulting in a bend in the distal section of the sheath, when an axial force is exerted on the core wire.

The movement restrictor may include a bond between the core wire and an inner wall of the sheath. The bond may be situated distally from the distal tip of the core wire. The bond may be formed by at least one of an adhesive or a weld. The movement restrictor may be a narrowing of an inner channel of the sheath. The movement restrictor may include an insert situated within an inner channel of the sheath. The insert may include at least one of an obstruction or a ring connected to a wall of the inner channel of the sheath. At least a portion of the sheath may include a coil including one or more wires wound to form a plurality of windings. At least some of the windings of the coil may form the distal portion of the sheath. At least some of the windings forming the distal portion of the sheath may be configured to have spaces therebetween. At least a portion of the proximal portion of the sheath may be formed of windings of the coil. At least some of the windings forming the proximal portion of the sheath may substantially lack spaces therebetween. The distal portion of the sheath may include a coil. At least a portion of the proximal portion of the sheath may be formed of a construct other than a coil. A portion of the core wire in the distal portion of the sheath may be configured such that repeated exertions of force on the core wire may result in repeatably consistent directional flexing of the core wire. The distal end portion of the core wire may have a non-circular cross-section that may be configured to enable preferential bending of the core wire. The loop of the core wire may include a double turn, such that following a turn of the core wire toward a proximal end of the sheath, the core wire may turn back toward the distal end of the sheath. The loop of the core wire maybe configured to form a gap between the loop of the core wire and an inner wall of the sheath. The gap may be sized such that a portion of the loop of the core wire maybe configured to distort within the gap when the core wire is subject to an applied force. The distortion of the core wire within the gap may include a buckling of the core wire within the gap. The loop of the core wire may be configured such that when the core wire is moved distally, at least a portion of the loop may not substantially move in a distal direction relative to the distal portion of the sheath. The intraluminal device may additionally include a mechanical step extending from the distal end portion of the core wire. The distal end portion of the core wire may be configured to engage a first surface of the movement restrictor and the mechanical step may be configured to engage a second surface of the movement restrictor that may be angled relative to the first surface of the movement restrictor. The intraluminal device may additionally include a widening situated proximally of the distal end portion. The widening of the core wire may be configured to engage the movement restrictor. The sheath and the core wire may be biased in a straight configuration and may be configured such that an axial pulling force on the core wire may cause bending of the distal bending segment of the sheath. The sheath may be configured to traverse vasculature within a human brain. The movement restrictor may include a step formed within an inner channel of the sheath. An edge of the distal end portion of the core wire may be positioned against the step. The core wire may be positioned against the step at a location distally spaced from the distal tip of the core wire. The loop of the core wire may be disjointed into two segments at a bend thereof and the disjointed segments of the core wire may be bonded together.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 1A illustrates an exemplary intraluminal device, consistent with various embodiments of the present disclosure.

FIGS. 1B-1E illustrate enlarged views of different segments of the intraluminal device of FIG. 1A, consistent with various embodiments of the present disclosure.

FIG. 1F illustrates the intraluminal device of FIG. 1A in a curved configuration, consistent with various embodiments of the present disclosure.

FIG. 2 illustrates an exemplary core wire of an intraluminal device, consistent with various embodiments of the present disclosure.

FIGS. 3B-3D illustrate cross-sectional views of the intraluminal device of FIG. 3A, consistent with various embodiments of the present disclosure.

FIG. 3F illustrates the intraluminal device distal portion of FIG. 3E in a first curved configuration, consistent with various embodiments of the present disclosure.

FIG. 7A illustrates the distal portion of an exemplary intraluminal device, consistent with various embodiments of the present disclosure.

FIG. 7B illustrates the intraluminal device of FIG. 7A in a curved configuration, consistent with various embodiments of the present disclosure.

DETAILED DESCRIPTION OF EMBODIMENTS

Figure 3A:
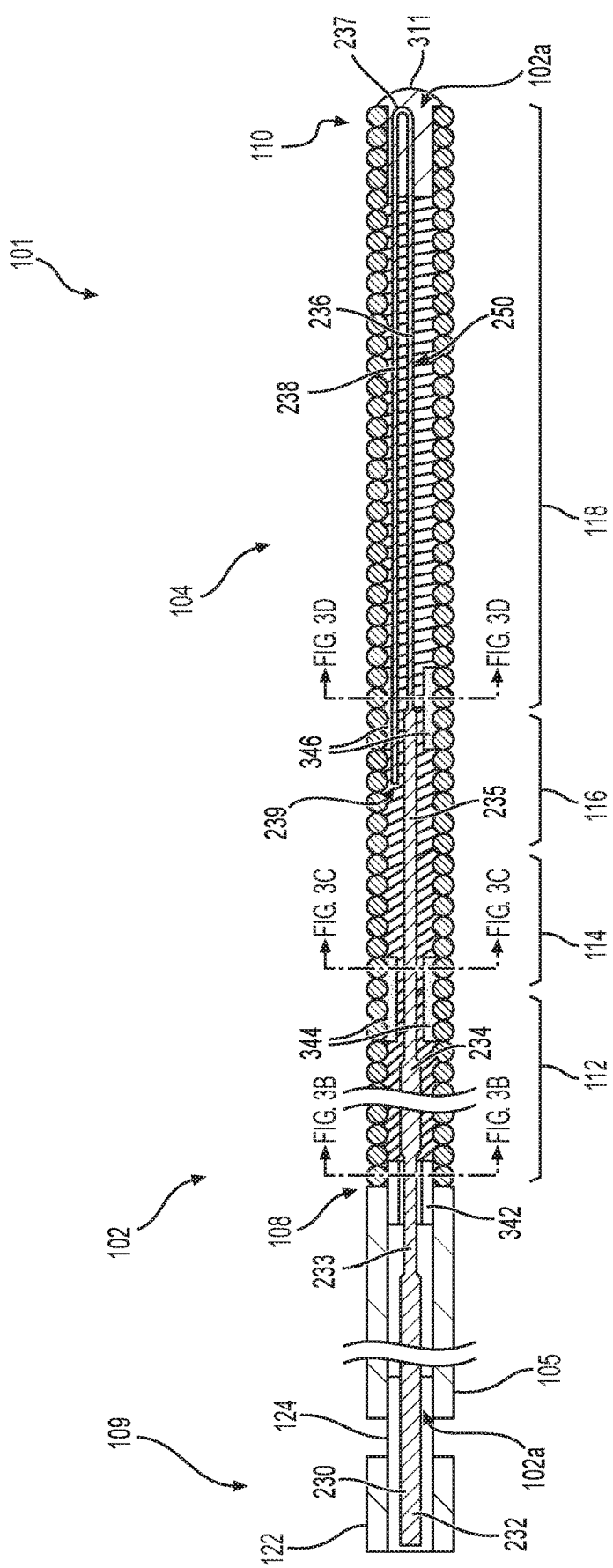
FIG. 3A illustrates an interior view of the intraluminal device of FIG. 1A, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Embodiments of the present disclosure relate generally to medical devices and methods of manufacturing medical devices. More particularly, embodiments of the present disclosure relate to intraluminal devices configured to navigate hollow body organs including, but not limited to, blood vessels and to guide delivery of diagnostic and/or therapeutic devices through the body. Additionally or alternatively, embodiments of the present disclosure may relate to methods of manufacturing intraluminal devices for navigating hollow body organs.

In accordance with embodiments of the present disclosure, there may be provided an intraluminal device including a core wire extending at least partially within the intraluminal device, the distal end of the core wire being bent or doubled back to form a loop within the intraluminal device. The looped core wire may provide improved steering and high torquability of the intraluminal device, while maintaining a soft and atraumatic tip.

FIG. 1A illustrates an exemplary intraluminal device 101 in a straightened configuration. Intraluminal device 101 may include a flexible, elongated sheath 102 that includes an elongated shaft 105 and a flexible, elongated coil 104 connected to the distal end of the elongated shaft 105. The elongated shaft 105 may be situated proximally from the coil 104; accordingly, the elongated shaft 105 may constitute a proximal section of the sheath 102 and the coil 104 may constitute a distal section of the sheath 102. Coil 104 may have a proximal end 108 and a distal end 110 and may be formed from a plurality of wires that are wound in a helical arrangement to form a hollow coil having at least one channel extending therethrough. Some or all of the wires of coil 104 may extend to the coil distal end 110, which may form the distal tip of the sheath 102. That is, coil 104 may terminate in a distal end of the elongated sheath 102. The wires of coil 104 may be made from Nitinol. In some embodiments, one or more wires of coil 104 may have an outer diameter of approximately 75 μm; alternatively, one or more wires of coil 104 may have an outer diameter larger or smaller than 75 μm. In some embodiments, coil 104 may have an axial length of between approximately 400 and 500 mm. For example, coil 104 may have an axial length of between approximately 430 mm and 440 mm.

The elongated shaft 105 may be formed of a construct other than a coil. For example, elongated shaft 105 may be a hollow, cylindrical hypotube constructed of an alloy or metal (e.g., nickel-titanium alloy (Nitinol)), stainless steel, a polymer (e.g., polyether ether ketone (PEEK)), a synthetic material (nylon, polyether block amide (PEBA)), and/or another suitable material. In some embodiments, elongated shaft 105 may have an outer diameter of between approximately 0.35 mm and 0.40 mm. For example, elongated shaft 105 may have an outer diameter of 0.35 mm, 0.36 mm, 0.37 mm, 0.38 mm, 0.39 mm, or 0.40 mm. In some embodiments, elongated shaft 105 may have an inner diameter of between approximately 0.20 mm and 0.25 mm. In some embodiments, elongated shaft 105 may have an axial length of between approximately 130 cm and 150 cm. For example, elongated shaft 105 may have an axial length of approximately 140 cm, 141 cm, or 142 cm.

Intraluminal device 101 may also include a handle 109 connected to the proximal end of the elongated shaft 105 that may be actuated by a user to steer the distal end of the elongated sheath 102. In some embodiments, handle 109 may include a user actuation segment 122 at its proximal end that is configured for movement relative to elongated shaft 105. A core wire (not pictured in FIG. 1A) may be connected to user actuation segment 122 and to the coil distal end 110. As illustrated in FIG. 1F, movement (e.g., axial movement) of the user actuation segment 122 relative to elongated shaft 105 may cause the core wire to exert a force on the coil distal end 110, causing straightening or bending of coil 104. In some embodiments, user actuation segment 122 may be cylindrical, with an outer diameter substantially equal to the outer diameter of elongated shaft 105. User actuation segment 122 may be at least partially hollow and may be constructed of an alloy or metal (e.g., nickel-titanium alloy), stainless steel, a polymer, and/or another suitable material. Although handle 109 is depicted as including a user actuation segment 122 in FIG. 1A, one of ordinary skill will understand that the exemplary handle may include any suitable mechanism for controlling bending and straightening of the elongated sheath 102, such as a wheel, a slider, a lever, a joystick, a touchpad, a rotatable cuff, or any other structure configured to control sheath bending and straightening.

In some embodiments, handle 109 may also include an inner member 124 situated at least partially within user actuation segment 122 and at least partially within elongated shaft 105. Inner member 124 may be connected to the user actuation segment 122 or to the elongated shaft 105 in order to guide and support the movement of the user actuation segment 122 relative to the elongated shaft 105. In some embodiments, inner member 124 may be configured as the locking inner member disclosed in WO 2019/116102 A2, which is incorporated herein by reference in its entirety.

In some embodiments, the exemplary coil 104 may be formed from a plurality of wires and may include two or more segments configured for different degrees of flexibility. For example, as illustrated in FIG. 1A, coil 104 may include a proximal segment 112, a first transition segment 114, a second transition segment 116, and a distal segment 118. In some embodiments, the proximal coil segment 112 may include the coil proximal end 108 and may be configured to be more rigid than the other segments of coil 104, such that the proximal coil segment 112 may be configured to transfer torque to the rest of the coil 104. The proximal coil segment 112 may be formed of a first number of wires, and the first number of wires required to form proximal coil segment 112 may be based on certain constraints. For example, certain constraints may include an outer diameter of the coil, an inner diameter of the coil, or an optimal coil angle for torque transfer. In some embodiments, proximal coil segment 112 may be formed of about six to 16 wires that are helically wound to form a coil. For example, proximal coil segment 112 may be formed of ten wires that are helically wound and that extend along the entire axial length of proximal coil segment 112. In some embodiments, proximal coil segment 112 may have an axial length of between approximately 400 mm and 425 mm. For example, proximal coil segment 112 may have an axial length of approximately 410 mm.

FIG. 1B illustrates an enlarged view of proximal coil segment 112. As shown, the wires of proximal coil segment 112 may be wound at a first coil angle $\alpha$, relative to the bottom planar surface of coil 104 and, thus, to the longitudinal axis of coil 104. In some embodiments, first coil angle $\alpha$ may be an angle of between 55° and 65°. In some embodiments, the number of wires used to form the proximal coil segment 112 may be selected based at least in part on the wire diameter and the diameter of a mandrel upon which the proximal coil segment 112 is formed, so as to achieve the desired first coil angle $\alpha$. For example, ten wires with outer diameters of 75 μm may be braided on a mandrel with an outer diameter of approximately 0.36 mm to form a proximal coil segment 112 having the desired first coil angle $\alpha$ of approximately 57°. As another example, nine wires with outer diameters of 85 μm may be braided on a mandrel with an outer diameter of approximately 0.36 mm to form a proximal coil segment 112 having the desired first coil angle $\alpha$ of approximately 56°.

Referring again to FIG. 1A, the coil 104 may additionally include at least two transition segments 114, 116 adjacent to the proximal coil segment 112. The transition segments 114 and 116 may be configured to provide a gradual increase in flexibility between the proximal coil segment 112 and the distal coil segment 118. In the embodiment illustrated in FIG. 1A, coil 104 may include two transition segments 114 and 116. In some alternative embodiments, coil 104 may include three transition segments, four transition segments, five transition segments, six transition segments, or any other suitable number of transition segments. The number of transition segments may vary based on various parameters, including rigidity of the proximal coil segment 112, flexibility of the distal coil segment 118, the axial length of the coil 104, or the number of wires used to form the coil 104.

The first transition segment 114 may be immediately adjacent to proximal coil segment 112 and may be formed from fewer wires than proximal coil segment 112, such that the first transition segment 114 may be configured for greater flexibility than proximal coil segment 112. In some embodiments, the first transition segment 114 may be formed from four to nine wires. For example, first transition segment 114 may be formed of six wires that are helically wound and that extend along the entire axial length of first transition segment 114. In some embodiments, the first transition segment 114 may have an axial length of between approximately 3.0 mm and 8.0 mm. For example, first transition segment 114 may have an axial length of approximately 5.0 mm.

FIG. 1C illustrates an enlarged view of the first transition segment 114. As shown, the wires of first transition segment 114 may be wound at a second coil angle $\beta$, relative to the bottom planar surface of coil 104 and, thus, to the longitudinal axis of coil 104. In some embodiments, second coil angle $\beta$ may be an angle of between 55° and 65° and may be larger than the first coil angle $\alpha$. In some embodiments, the number of wires used to form the first transition segment 114 may be selected based at least in part on the wire diameter and the diameter of a mandrel upon which the first transition segment 114 is formed, so as to achieve the desired second coil angle $\beta$. For example, six wires with outer diameters of 75 μm may be braided on a mandrel with an outer diameter of approximately 210 μm to form a first transition segment 114 having the desired second coil angle $\beta$ of approximately 60°.

Referring again to FIG. 1A, the second transition segment 116 may be immediately adjacent to the first transition segment 114 and may be formed from fewer wires than first transition segment 114, such that the second transition segment 116 may be configured for greater flexibility than first transition segment 114. In some embodiments, the second transition segment 116 may be formed from three to eight wires. For example, second transition segment 116 may be formed of four wires that are helically wound and that extend along the entire axial length of second transition segment 116. In some embodiments, the second transition segment 116 may have an axial length of between approximately 3.0 mm and 8.0 mm. For example, second transition segment 116 may have an axial length of approximately 5.0 mm. In some embodiments, first transition segment 114 and second transition segment 116 may have the same axial length.

FIG. 1D illustrates an enlarged view of the second transition segment 116. As shown, the wires of second transition segment 116 may be wound at a third coil angle γ, relative to the bottom planar surface of coil 104 and, thus, to the longitudinal axis of coil 104. In some embodiments, third coil angle γ may be an angle of between 65° and 75° and may be larger than the second coil angle β. In some embodiments, the number of wires used to form the second transition segment 116 may be selected based at least in part on the wire diameter and the diameter of a mandrel upon which the second transition segment 116 is formed, so as to achieve the desired third coil angle γ. For example, four wires with outer diameters of 75 μm may be braided on a mandrel with an outer diameter of approximately 210 μm to form a second transition segment 116 having the desired third pitch angle γ of approximately 70°.

Referring against to FIG. 1A, the distal coil segment 118 may be immediately adjacent to the second transition segment 116 and may include the coil distal end 110. Distal coil segment 118 may be configured to be very flexible such that the distal coil segment 118 may be atraumatic as intraluminal device 101 is advanced through the body. In some embodiments, distal coil segment 118 may be more flexible than the other segments of coil 104, including second transition segment 116. Distal coil segment 118 may be formed of about one to four wires. For example, distal coil segment 118 may be formed of one wire or of two wires that are helically wound into a coil. Advantageously, forming the distal coil segment 118 from between one to four wires (e.g., from two wires) may provide a soft and atraumatic distal coil segment 118, while still maintaining the ability of distal coil segment 118 to transmit torque applied to the proximal end of intraluminal device 101. In some embodiments, distal coil segment 118 may have an axial length of between approximately 15 mm and 25 mm. For example, distal coil segment 118 may have an axial length of approximately 20 mm. Due to the decreasing number of wires between the different segments of coil 104, the flexibility of the coil 104 may gradually increase in a longitudinal direction from the coil proximal end 108 to the coil distal end 110. Advantageously, the decreasing number of wires in coil 104 may achieve rigidity at proximal coil segment 112, relative to distal coil segment 118, and flexibility at distal coil segment 118, relative to proximal coil segment 112. In addition, rigidity may gradually decrease in the longitudinal direction from proximal coil segment 112 to distal coil segment 118.

FIG. 1E illustrates an enlarged view of the distal coil segment 118. As shown, the wires of distal coil segment 118 may be wound at a fourth coil angle θ, relative to the bottom planar surface of coil 104 and, thus, to the longitudinal axis of coil 104. In some embodiments, fourth coil angle θ may be an angle of between 77° and 83° and may be larger than the third coil angle γ. In some embodiments, the number of wires used to form the distal coil segment 118 may be selected based at least in part on the wire diameter and the diameter of a mandrel upon which the distal coil segment 118 is formed, so as to achieve the desired fourth coil angle θ. For example, two wires with outer diameters of 75 μm may be braided on a mandrel with an outer diameter of approximately 210 μm to form a distal coil segment 118 having the desired fourth pitch angle θ of approximately 80°.

In addition to decreasing the number of wires along coil 104, the coil angle at which the wires are wound may vary from proximal coil segment 112 to distal coil segment 118. The variation in coil angle may allow the transfer of maximum torque from the proximal coil segment 112 to the rest of coil 104, while also maintaining the desired flexibility of distal coil segment 118 and the structural strength of the entire intraluminal device 101. In some embodiments, the coil angle at which the wires are wound to form coil 104 may increase gradually from proximal coil segment 112 to distal coil segment 118. For example, the second coil angle β may be larger than the first coil angle α. Additionally, or alternatively, the third coil angle γ may be larger than the second coil angle β. Additionally, or alternatively, the fourth coil angle θ may be larger than the third coil angle γ. Advantageously, an increase in the coil angle may increase the flexibility of the corresponding section of coil 104. Distal coil segment 118 may have the largest coil angle and may accordingly be the most flexible segment of coil 104; in some embodiments, the distal coil segment 118 may constitute a distal bending segment of coil 104. Similarly, proximal coil segment 112 may have the smallest coil angle and may accordingly be the most rigid segment of coil 104; in some embodiments, the proximal coil segment 112 may constitute a proximal support segment of coil 104.

In the embodiment illustrated in FIG. 1A, coil 104 may have a constant diameter along its entire axial length. For example, proximal coil segment 112, first transition segment 114, second transition segment 116, and distal coil segment 118 may have a constant outer diameter of between approximately 0.35 mm and 0.40 mm, for example, an outer diameter of 0.35 mm, 0.36 mm, 0.37 mm, 0.38 mm, 0.39 mm, or 0.40 mm. In some alternative embodiments, the diameter of coil 104 may gradually decrease from proximal coil segment 112 to distal coil segment 118. For example, proximal coil segment 112 may have an outer diameter of between approximately 0.35 mm and 0.40 mm, and distal coil segment 118 may have an outer diameter of between approximately 0.32 mm and 0.38 mm. Advantageously, the reduced diameter of distal coil segment 118 may enable the distal segment to have a desired flexibility that is greater than the flexibility of proximal coil segment 112.

FIG. 1F illustrates an exemplary configuration of intraluminal device 101 in which at least a portion of coil 104 is bent into a curved configuration. In some embodiments, some or all of the distal coil segment 118 may be configured to bend into the curved configuration. As shown in FIG. 1F, axial movement of the user actuation segment 122 relative to elongated shaft 105 may effect radial bending of the coil 104 (including at least a portion of distal coil segment 118) from a straight configuration (e.g., the configuration illustrated in FIG. 1A) into a curved or angled configuration, or from a curved or angled configuration to a straight configuration or into a different curved or angled configuration. In some embodiments, the bending segment of coil 104 may be configured to bend in a single direction from the straight configuration (e.g., from a straight configuration towards a left-hand side, but not towards a right-hand side) due to the actuation of handle 109. In other embodiments, the bending segment of coil 104 may be configured to bend in two opposite directions from the straight configuration (e.g., both to the left-hand side and the right-hand side from the straight configuration) due to the actuation of handle 109.

FIG. 2 illustrates an exemplary elongated core wire 230 of an intraluminal device. Core wire 230 may extend between a proximal tip 231 and a distal tip 239. In some embodiments, core wire 230 may be situated at least partially within the sheath 102 of intraluminal device 101 to control bending and straightening of coil 104. The control wire 230 may be constructed of an alloy or metal (e.g., nickel-titanium alloy, or Nitinol), stainless steel, a polymer, and/or another suitable material, and may have a polytetrafluoroethylene (PTFE) coating. In some embodiments, core wire 230 may include portions having different cross-sectional shapes and/or dimensions. For example, core wire 230 may include portions 232 and 234 with circular cross-sections and portions 233 and 235 in which the cross-sectional area of the core wire is reduced, relative to portions 232 and 234. As illustrated in FIG. 2, core wire portion 234 may be situated distally from core wire portion 232. In some embodiments, core wire portions 232 and 234 may have circular cross-sections, with outer diameters of between approximately 0.12 mm and 0.18 mm. For example, one or both of core wire portions 232 and 234 may have an outer diameter of approximately 0.15 mm. In some embodiments, core wire portion 232 may have an axial length of between approximately 140 cm and 155 cm. Additionally, or alternatively, core wire portion 234 may have an axial length of between approximately 350 mm and 405 mm.

In some embodiments, core wire portions 233 and 235 may have cross-sections that are non-circular (e.g., elliptical, oval-shaped, rectangular, etc.) and may have smaller cross-sectional areas than core wire portions 232 and 234. For example, in some embodiments core wire portions 233 and 235 may be formed by selectively flattening or otherwise deforming portions of core wire 230. In some alternative embodiments, the non-circular portions 233 and 235 may be formed by adhesion of additional materials to portions of core wire 230 to form a non-round shape. As illustrated in FIG. 2, core wire portion 235 may be situated distally from core wire portion 233. Although core wire 230 is depicted as including two non-circular portions 233 and 235 in FIG. 2, one of ordinary skill will understand that the exemplary core wire may include any suitable number of non-circular portions, such as zero portions, one portion, three portions, four portions, or five portions. In some embodiments, core wire portion 233 may have an axial length of between approximately 30 mm and 45 mm (e.g., an axial length of approximately 40 mm). Additionally, or alternatively, core wire portion 235 may have an axial length of between approximately 20 mm and 30 mm (e.g., an axial length of approximately 26 mm). In some embodiments, core wire portion 235 may have a shorter axial length than core wire portion 233, and approximately 400 mm of the core wire 230 may be provided between the distal end of core wire portion 235 and the distal end of core wire portion 233.

As illustrated in FIG. 2, core wire 230 may additionally include a distal end portion 250, which may be adjacent to core wire portion 235 and may extend to, and include, the distal tip 239 of the core wire. The core wire distal end portion 250 may have an axial length of between approximately 30 mm and 50 mm (e.g., an axial length of approximately 40 mm). In some embodiments, a first dimension of core wire 230 (referred to hereafter as height) may be smaller in core wire distal end portion 250 than in any other portion of the core wire. In some embodiments, the core wire distal end portion 250 may have a smaller cross-sectional area than the rest of the core wire.

Although the core wire distal end portion 250 is depicted in FIG. 2 as including a bend 237, the core wire 230 (including core wire distal end portion 250) may be biased in a straightened configuration. In some embodiments, core wire distal end portion 250 may be flexible such that core wire distal end portion 250 may be bent or doubled back to form a core wire bend 237, at which the core wire 230 may change from a distal axial direction (e.g., to the right in FIG. 2) to a proximal axial direction (e.g., to the left in FIG. 2). The core wire distal end portion 250 may include a first loop portion 236 extending between core wire portion 235 and bend 237 and a second loop portion 238 extending between bend 237 and distal tip 239. In the configuration of FIG. 2, the core wire bend 237 may be formed such that first loop portion 236 and second loop portion 238 may have approximately equal axial lengths. For example, first loop portion 236 and second loop portion 238 may both have an axial length of approximately 20 mm.

FIG. 3A illustrates an interior view of intraluminal device 101 in the straightened configuration. The elongated sheath 102 (i.e., elongated shaft 105 and coil 104) may have an inner channel 102a extending from the proximal end of elongated shaft 105 to the coil distal end 110. Inner channel 102a may be formed by the inner lumens of elongated shaft 105 and coil 104. As shown in FIG. 3A, core wire 230 may be situated within intraluminal device 101 in the bent configuration illustrated in FIG. 2. The proximal end of core wire 230 may be secured to a portion of handle 109 (e.g., user actuation segment 122). Core wire 230 may extend through the inner channel 102a of the elongated sheath 102 to a location at or near the coil distal end 110; as a result, the core wire distal end portion 250 may be situated at least partially within the distal coil segment 118. In some embodiments, core wire 230 may be situated within the intraluminal device 101 such that the core wire bend 237 may be situated at or near the coil distal end 110. Accordingly, the core wire bend 237 may constitute the distal-most portion of the core wire 230. The second loop portion 238 may extend proximally from the core wire bend 237 so that the core wire distal tip 239 may be situated proximally from bend 237 and from the coil distal end 110. In some embodiments, the core wire bend 237 may be encompassed within a dome cap 311, which may be constructed of epoxy and may be rounded to prevent injury to tissue. Dome cap 311 may be formed, in part, by filling the inner channel 102a of the sheath with epoxy near the coil distal end 110, such that the epoxy covers the core wire bend 237 and contacts the walls of the inner channel 102a. Accordingly, dome cap 311 may bond the core wire bend 237 to the coil distal end 110.

In the embodiment of FIG. 3A, elongated shaft 105 and coil 104 may have substantially equal outer diameters, with the outer diameter remaining substantially constant between the proximal and distal ends of the elongated sheath 102. For example, the elongated sheath 102 may have a constant outer diameter of between approximately 0.30 mm and 0.40 mm (e.g., an outer diameter of approximately 0.36 mm). In some alternative embodiments, certain portions of elongated sheath 102 may have smaller outer diameters than other portions of elongated sheath 102. For example, the outer diameter of coil 104 may gradually decrease from proximal coil segment 112 to distal coil segment 118, with proximal coil segment 112 having a larger outer diameter than first transition segment 114, first transition segment 114 having a larger outer diameter than second transition segment 116, and second transition segment 116 having a larger outer diameter than distal coil segment 118. Advantageously, the decrease in outer diameter may provide greater flexibility at the distal coil segment 118, while the proximal coil segment 112 remains more rigid than the other segments of the coil.

FIG. 3B illustrates a cross-sectional view of intraluminal device 101 at the coil proximal end 108, near the location at which the elongated shaft 105 is connected to the proximal coil segment 112. A portion of core wire portion 233 may extend through the coil proximal end 108. As illustrated in FIG. 3B, core wire portion 233 may have a non-circular cross-section, with the height of core wire portion 233 being smaller than a second dimension of core wire portion 233 that is perpendicular to the height (referred to hereafter as width). In some embodiments, core wire portion 233 may have a height of between approximately 0.10 mm and 0.15 mm. For example, core wire portion 233 may have a height of approximately 0.12 mm. Additionally, or alternatively, core wire portion 233 may have a width of approximately 0.15 mm.

As shown in FIG. 3B, proximal coil segment 112 may include between six wires and 16 wires (e.g., ten wires) wound into a helical coil with inner channel 102*a* formed in the center of the coil. Core wire portion 233 may extend through the portion of proximal coil segment 112 depicted in FIG. 3B. Optionally, an anti-rotation mechanism may be provided at or near the coil proximal end 108 to prevent axial rotation between the core wire 230 and the sheath 102, without preventing relative axial movement between the core wire 230 and the sheath 102. In the embodiment of FIG. 3B, an internal connector 342 may be provided at the coil proximal end 108, extending along the inner channel 102*a* between the elongated shaft 105 and coil 104. An adhesive or bonding material 343 (e.g., PEEK) may be provided in the spaces between internal connector 342 and the elongated shaft 105 and/or in the spaces between internal connector 342 and the proximal coil segment 112. Thus, internal connector 342 may secure the elongated shaft 105 and coil 104 together.

Internal connector 342 may be a hollow tube constructed of an alloy or metal (e.g., nickel-titanium alloy, or nitinol), stainless steel, a polymer, and/or another suitable material. In some embodiments, internal connector 342 may have an axial length of between approximately 3.0 mm and 30 mm. For example, internal connector 342 may have an axial length of between approximately 4.0 mm and 16 mm. In some embodiments, internal connector 342 may have an outer diameter of approximately 0.20 mm and an inner diameter of approximately 0.16 mm. In some embodiments, internal connector 342 may have an elliptical or oval-shaped cross-section (as shown in FIG. 3B) through which the core wire portion 233 may extend. Internal connector 342 and core wire portion 233 may both include non-circular cross-sections with respective heights that are smaller than their respective widths. In addition, the inner diameter of internal connector 342 may be slightly larger than the outer diameter of core wire portion 233, such that a space 348 may be provided between the internal connector 342 and core wire portion 233. As a result, internal connector 342 and core wire portion 233 may resist axial rotation of the core wire 230 relative to the sheath 102, while permitting axial movement of the core wire 230 relative to the sheath 102. Additionally, or alternatively, a different anti-rotation mechanism may be provided at or near the coil proximal end 108 to prevent axial rotation between the core wire 230 and sheath 102. Advantageously, the addition of one or more anti-rotation mechanisms within the inner channel 102*a* may prevent the core wire 230 from twisting within the elongated sheath 102 and maintain a 1:1 ratio of force transmission from the core wire 230 to the coil distal end 110.

FIG. 3C illustrates a cross-sectional view of intraluminal device 101 along the first transition segment 114 of the coil. First transition segment 114 of the coil may include between four wires and nine wires (e.g., six wires) wound into a helical coil with inner channel 102*a* formed in the center of the coil. Core wire portion 235 may extend through the portion of the first transition segment 114 depicted in FIG. 3C. As illustrated in FIG. 3C, core wire portion 235 may have a non-circular cross-section, with the height of core wire portion 235 being smaller than the width of core wire portion 235. In some embodiments, core wire portion 235 may have a height of between approximately 0.10 mm and 0.15 mm. For example, core wire portion 235 may have a height of approximately 0.12 mm. Additionally, or alternatively, core wire portion 235 may have a width of approximately 0.15 mm.

In some embodiments, an anti-rotation mechanism may be provided within the first transition segment 114, so as to prevent axial rotation of the core wire 230 relative to the coil 104 without preventing relative axial movement between the core wire 230 and the coil 104. For example, a movement restrictor 344 may be provided at least partially within the first transition segment 114 as an anti-rotation mechanism. The movement restrictor 344 may include a polymer (e.g., PEEK), an adhesive, a weld, and/or any other suitable material. The material of movement restrictor 344 may be inserted through coil 104 to form a non-round cross-section of the inner lumen of the first transition segment 114. In some embodiments, the material of movement restrictor 344 may be placed at two locations along the wall of inner channel 102*a*, the two locations being situated approximately 180° apart. As illustrated in FIG. 3C, movement restrictor 344 may be adjacent to the long edges of the cross-section of core wire portion 235 (i.e., the top and bottom edges of core wire portion 235 in FIG. 3C). In some alternative embodiments, the material of movement restrictor 344 may be placed at more or fewer locations along the wall of inner channel 102*a*. The placement of movement restrictor 344 within inner channel 102*a* may prevent the non-circular core wire portion 235 from rotating within the first transition segment 114, while relative axial movement between the core wire portion 235 and the first transition segment 114 may remain unimpeded. In some alternative embodiments, the first transition segment 114 of the coil may be provided without an anti-rotation mechanism. In such embodiments, the core wire 230 may have a round cross-sectional shape within the first transition segment 114, similar to core wire portions 232 and 234.

FIG. 3D illustrates a cross-sectional view of intraluminal device 101 along the distal coil segment 118. As shown, the distal coil segment 118 may include between one wire and four wires (e.g., two wires) wound into a helical coil with inner channel 102*a* formed in the center of the coil. The cross-sectional view of FIG. 3D may depict a segment of coil 104 in which the core wire distal end portion 250 may be situated. Accordingly, the first loop portion 236 and second loop portion 238 of the core wire may both extend through the portion of distal coil segment 118 depicted in FIG. 3D. In some embodiments, the core wire distal end portion 250 (including first loop portion 236 and second loop portion 238) may have a height of between approximately 0.030 mm and 0.040 mm. For example, the core wire distal end portion 250 may have a height of approximately 0.036 mm. Additionally, or alternatively, the core wire distal end portion 250 may have a width of between approximately 0.05 mm and 0.15 mm. For example, the core wire distal end portion 250 may have a width of approximately 0.11 mm.

In some embodiments, a movement restrictor 346 may be provided within the distal coil segment 118 to prevent axial rotation of the core wire 230 relative to the coil 104 without preventing relative axial movement between the core wire 230 and the coil 104. For example, a movement restrictor 346 with a similar configuration as movement restrictor 344 of FIG. 3C may be provided at least partially within the distal coil segment 118 as an anti-rotation mechanism. The movement restrictor 346 may include a polymer (e.g., PEEK), an adhesive, a weld, and/or any other suitable material. The material of movement restrictor 346 may be inserted through coil 104 and may be situated at least partially within inner channel 102*a*; accordingly, movement restrictor 346 may form a narrowing of inner channel 102*a*. In the configuration of FIG. 3D, first loop portion 236 of the core wire may be situated in the center of the inner channel 102*a*, such that the first loop portion 236 is not in contact with the distal coil segment 118 or movement restrictor 346. Second loop portion 238 may be situated in closer proximity to distal coil segment 118 and at least one surface of second loop portion 238 may be positioned against, and in contact with, the movement restrictor 346. In some embodiments, movement restrictor 346 may protrude into inner channel 102*a* to form a step, with the at least one surface of the second looped portion 238 configured to be positioned against the step. The movement restrictor 346 may bond the second loop portion 238 of the core wire to a wall of inner channel 102*a*, thus preventing relative axial and rotational movement between the sheath 102 and second loop portion 238 and distal tip 239. Thus, movement restrictor 346 may be configured both as an anti-rotation mechanism for core wire 230 and as a bond between the second loop portion 238 and the distal coil segment 118. Because the second loop portion 238 of the core wire may extend proximally beyond the movement restrictor 346, the bond between the core wire and inner wall of the sheath may be situated distally from distal tip 239 of the core wire.

In some alternative embodiments, movement restrictor 346 may include an insert situated within inner channel 102*a* of the sheath. For example, movement restrictor 346 may have a similar configuration as internal connector 342 or another ring-shaped insert and may be connected to the wall of inner channel 102*a*. Additionally, or alternatively, the insert of movement restrictor 346 may be configured as a partial obstruction within sheath 102 that is connected to the wall of inner channel 102*a*.

Figure 3E:
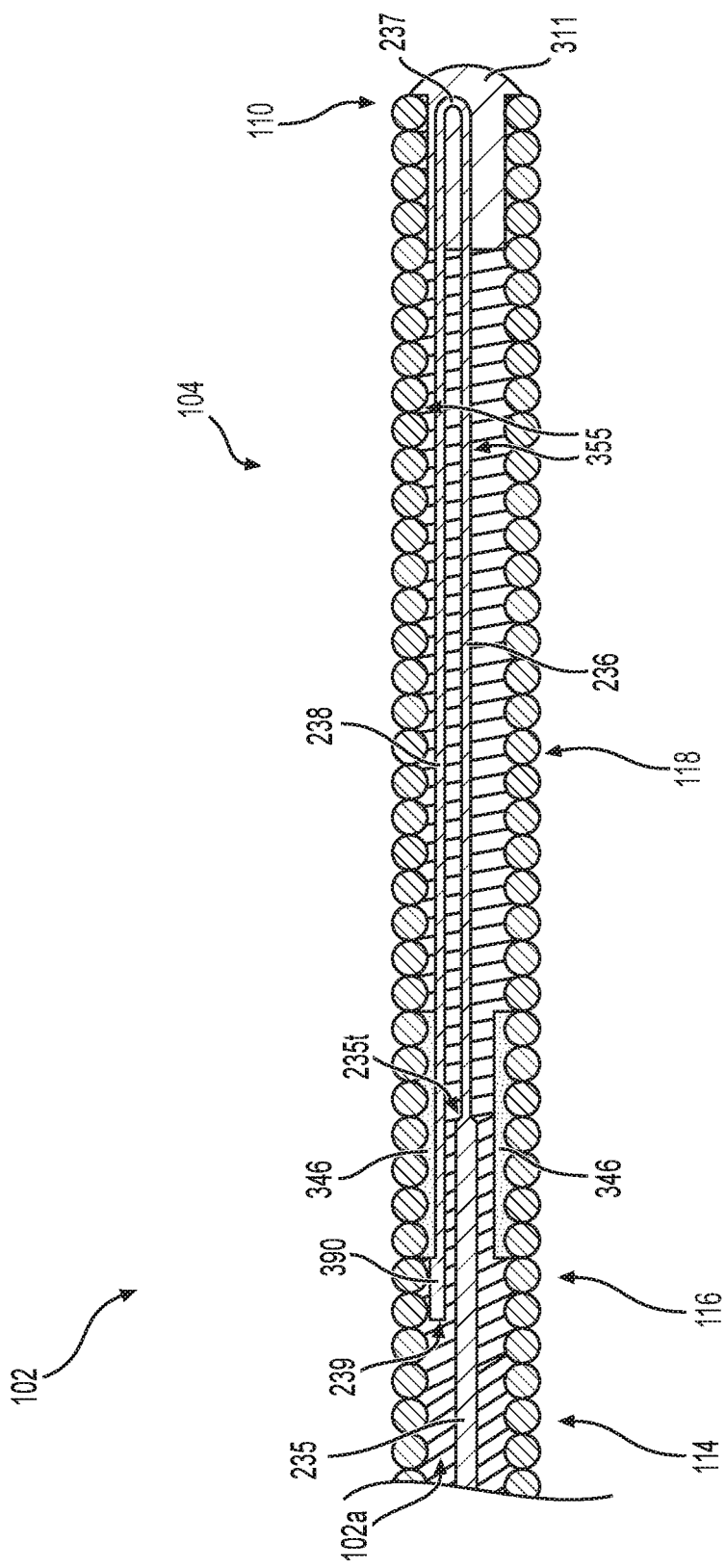
FIG. 3E illustrates an enlarged view of a distal portion of the intraluminal device of FIG. 3A, consistent with various embodiments of the present disclosure.

FIG. 3E illustrates an enlarged view of a distal portion of the intraluminal device 101 in the straightened configuration. In some embodiments, sheath 102 may be biased in the straightened configuration of FIG. 3E and at least a portion of coil 104 (e.g., distal coil segment 118) may be configured to bend when an axial pulling force is exerted on core wire 230. Core wire 230 may be bonded to sheath 102 by dome cap 311 and by movement restrictor 346; apart from these two points of connection, core wire 230 may be configured for movement relative to sheath 102. As shown in FIG. 3E, second loop portion 238 of the core wire may be provided between first loop portion 236 and distal coil segment 118. However, when intraluminal device 101 is in the straight configuration depicted in FIG. 3E, second loop portion 238 may be spaced apart from distal coil segment 118 such that a gap may be provided between the second loop portion 238 and the walls of inner channel 102*a*. Movement restrictor 346 and dome cap 311 may both extend between coil 104 and core wire 230, thus bonding the coil and core wire together. In some embodiments, core wire bend 237 may be situated evenly with the distal end 110 of the coil. Alternatively, core wire bend 237 may be situated proximally from coil distal end 110.

As shown in FIG. 3E, the second loop portion 238 may extend proximally beyond movement restrictor 346. As a result, distal tip 239 of the core wire may be situated proximally from movement restrictor 346. Optionally, a mechanical step 390 may be provided in the portion of second loop portion 238 extending proximally beyond movement restrictor 346. Step 390 may include material added to the surface of second loop portion 238 that faces coil 104 (e.g., upwards in FIG. 3E) so that the core wire may be in contact with a side surface of movement restrictor 346 (e.g., the left vertical surface of movement restrictor 346 in FIG. 3E) while the more distal section of second loop portion 238 may be in contact with an axially-oriented surface of movement restrictor 346 (e.g., the lower surface of movement restrictor 346 in FIG. 3E). Accordingly, the portion of second loop portion 238 including a mechanical step 390 may have a larger cross-sectional area than portions of second loop portion 238 without a mechanical step. Advantageously, when core wire 230 is pulled axially, step 390 may push against the adjacent surface of movement restrictor 346, thus providing further resistance against movement of the core wire relative to movement restrictor 346. Accordingly, step 390 may increase the bonding force between core wire 230 and movement restrictor 346. In some alternative embodiments, distal tip 239 may be placed in contact with movement restrictor 346.

In some embodiments, the transition 235*t* between core wire portion 235 and the core wire distal end portion 250 may be situated between the proximal and distal ends of movement restrictor 346 while intraluminal device 101 is in the straight configuration depicted in FIG. 3E. In addition, gaps 355 may be formed between the wall of inner channel 102*a* and the first loop portion 236 and second loop portion 238. That is, apart from the connections between core wire 230 and coil 104 formed by movement restrictor 346 and dome cap 311, the rest of core wire distal end portion 250 may be spaced apart from the walls of inner channel 102*a* when the intraluminal device is in the straight configuration, thus forming gaps 355.

FIG. 3F illustrates the distal portion of intraluminal device 101 in a first curved configuration. The curved configuration of FIG. 3F may be effected by application of a proximally-directed force on core wire 230 (which may be caused, for example, by proximal movement of user actuation segment 122 relative to sheath 102). Due to its relatively small cross-sectional area, core wire distal end portion 250 may have a lower moment of inertia relative to the rest of the core wire. As a result, axial force application on core wire 230 may cause first loop portion 236 and second loop portion 238 of the core wire to buckle from their respective straightened configurations into curved configurations, without other portions of core wire 230 buckling. Due to the bonds between core wire distal end portion 250 and coil 104 that are formed by dome cap 311 and by movement restrictor 346, buckling of first loop portion 236 and second loop portion 238 may force the distal portion of coil 104 to radially bend from the straight configuration of FIG. 3E into the curved configuration of FIG. 3F. In some embodiments, movement restrictor 346 may be configured as a hinge of core wire distal end portion 250 by permitting rotation of second loop portion 238 but preventing axial movement of second loop portion 238. As a result, first loop portion 236 and second loop portion 238 may buckle under lower applied axial forces, compared to a configuration in which the end of second loop portion 238 was fixed against rotation. Advantageously, the hinge of movement restrictor 346 may improve steerability of distal coil end 110 by reducing the magnitude of force needed to cause bending of the distal end of intraluminal device 101.

In some embodiments, the entire length of coil 104 distal to movement restrictor 346 may bend due to axial force application on core wire 230. As a result, some or all of distal coil segment 118 may be configured to bend due to axial force application on core wire 230. Dome cap 311 may secure core wire bend 237 against movement relative to coil distal end 110. Similarly, movement restrictor 346 may secure the portion of second loop portion 238 that is in contact with movement restrictor 346 against movement relative to the portion of coil 104 that is in contact with movement restrictor 346. However, the sections of first loop portion 236 and second loop portion 238 between dome cap 311 and movement restrictor 346 may freely move within coil 104 and may buckle or otherwise distort into gaps 355 within the coil when a force is applied to core wire 230. In addition, and as illustrated in FIG. 3F, the proximal movement of core wire 230 may pull core wire transition 235t in a proximal direction relative to sheath 102. In some embodiments, core wire distal end portion 250 may be configured such that repeated exertions of force on core wire 230 (e.g., pulling core wire 230 in a proximal direction) may result in consistent directional flexing of the core wire 230. This may be due to the bonds between core wire 230 and sheath 102 that are formed by dome cap 311 and movement restrictor 346, as well as to the non-circular cross-sectional shape of core wire distal end portion 250. Specifically, due to the aforementioned shape and the placement of core wire distal end portion 250 within coil 104, core wire distal end portion 250 may preferentially buckle into the configurations thereof depicted in FIGS. 3F and 3G when proximally-directed and distally-directed forces, respectively, are exerted on core wire 230.

Figure 3G:
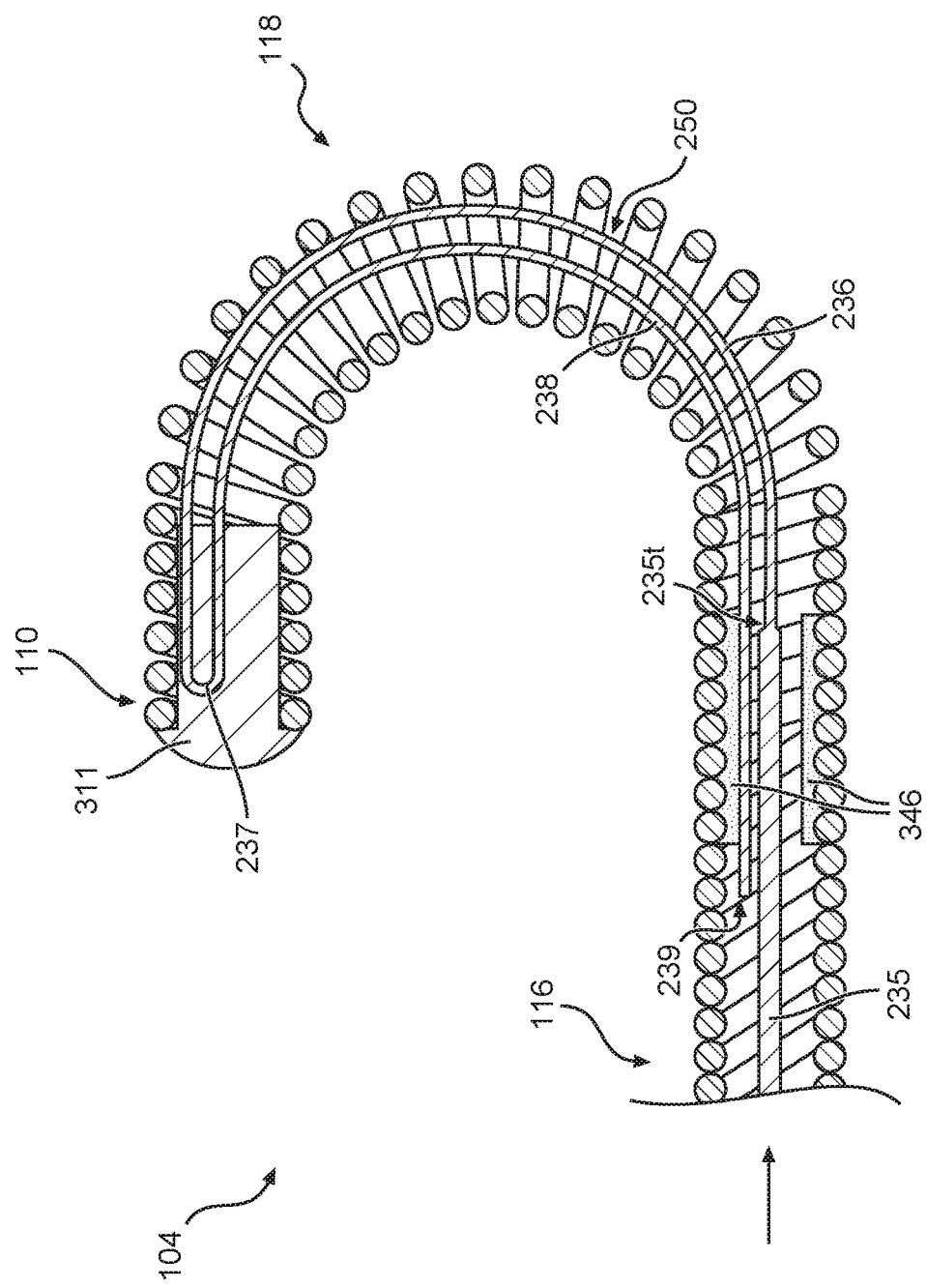
FIG. 3G illustrates the intraluminal device distal portion of FIG. 3E in a second curved configuration, consistent with various embodiments of the present disclosure.

FIG. 3G illustrates the distal portion of intraluminal device 101 in a second curved configuration in which coil 104 radially bends in an opposite direction from the configuration of FIG. 3F. The curved configuration of FIG. 3G may be effected by application of a distally-directed force on core wire 230 (e.g., due to distal movement of user actuation segment 122 relative to sheath 102). The distal force application on core wire 230 may cause first loop portion 236 and second loop portion 238 to buckle in a direction opposite from the buckling direction of FIG. 3F. The buckling of first loop portion 236 and second loop portion 238 may force the distal portion of coil 104 to radially bend in a second bending direction opposite from the bending direction of FIG. 3F (i.e., upwards in FIG. 3G, compared with downwards in FIG. 3F). As illustrated in FIG. 3G, the distal movement of core wire 230 may push the core wire transition 235t in a distal direction relative to sheath 102.

Advantageously, looped core wire 230 may reduce the magnitude of force required to effect bending of the distal end of intraluminal device 101. Specifically, the low moment of inertia of core wire distal end portion 250, combined with the hinge of movement restrictor 346 and the arrangement of core wire portions 236 and 238 within coil distal segment 118, may enable core wire distal end portion 250 to buckle (and, thus, enable bending of intraluminal device 101) under the application of less than half the force that is required to bend intraluminal devices known in the art that do not incorporate a looped core wire. As a result, the looped core wire 230 may provide more exact steering of the distal end of intraluminal device 101, since less force is required to bend the distal end of intraluminal device 101 into a desired curved configuration. In addition, intraluminal device 101 may have a soft, atraumatic tip due to the coil arrangement in distal coil segment 118 and the configuration of dome cap 311 as a rounded, atraumatic edge of intraluminal device 101. Accordingly, intraluminal device 101 may be easily maneuvered through narrow, tortuous lumens of the body (such as intracranial vessels) due to the improved steering provided by looped core wire 230, without causing injury to the surrounding anatomy.

Figure 4:
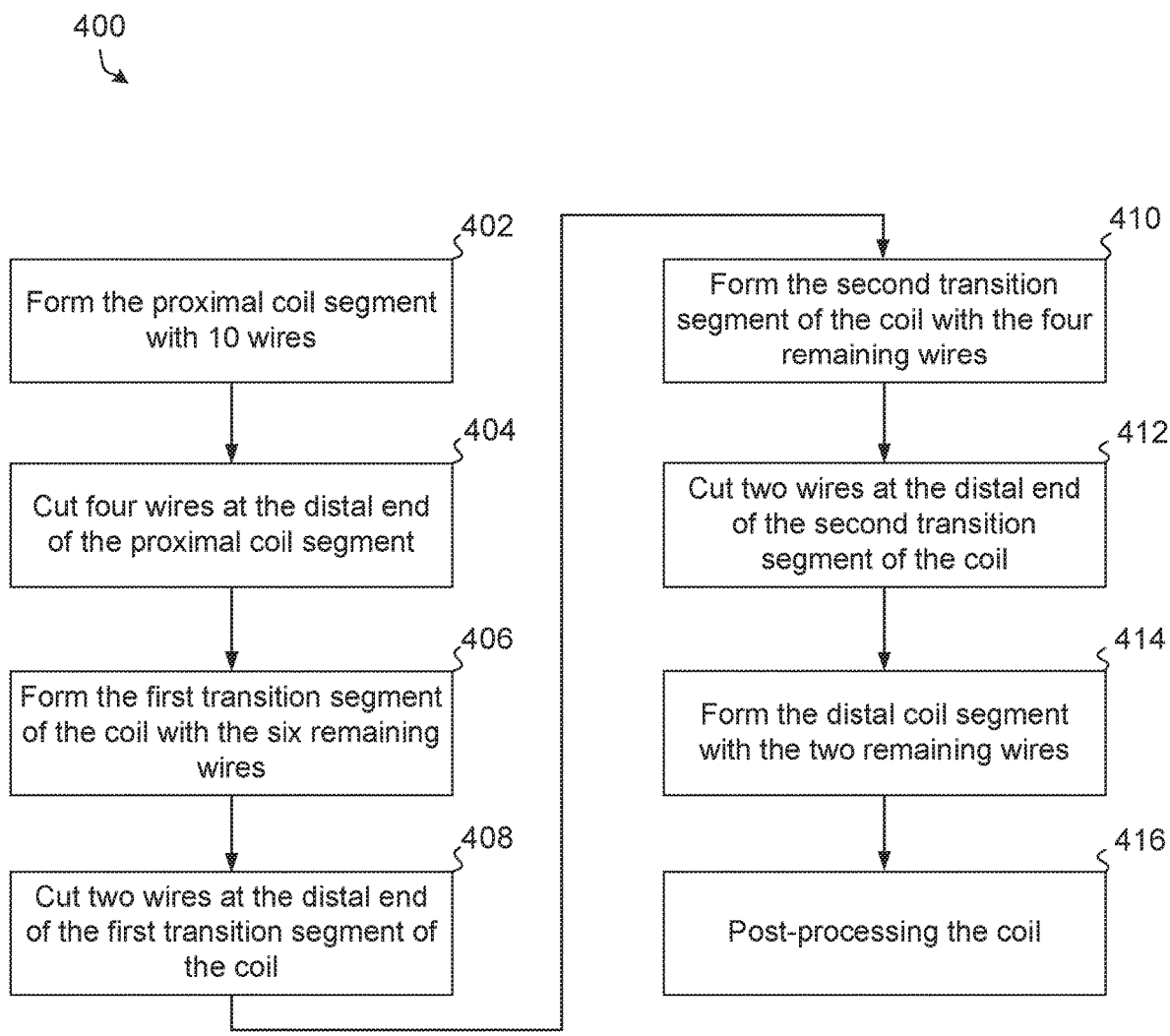
FIG. 4 illustrates an exemplary method of manufacturing an elongated coil of an intraluminal device, consistent with various embodiments of the present disclosure.

FIG. 4 illustrates an exemplary method 400 of manufacturing an elongated coil of an intraluminal device. One of ordinary skill will understand that manufacturing method 400 disclosed herein is merely exemplary and that other methods could be used to manufacture elongated coils of an intraluminal devices as disclosed herein. Moreover, exemplary method 400 may be used to manufacture any suitable coil of an intraluminal device, including and not limited to coil 104 of intraluminal device 101. Although the exemplary method 400 as disclosed herein describes the manufacturing of an elongated coil with a proximal coil segment, a distal coil segment, and two transition segments between the proximal and distal coil segments, one of ordinary skill will understand that an elongated coil with any suitable number of transition segments may be manufactured according to method 400, with at least one parameter of the coil (e.g., number of wires, wire material(s), wire gauge, coil diameter, spacing between individual wires, and/or spacing between groups of wires) differing between each coil segment. For example, an exemplary coil manufactured according to method 400 may include one transition segment, three transition segments, four transition segments, five transition segments, six transition segments, seven transition segments, eight transition segments, or any other suitable number of transition segments between the proximal and distal segments of the coil.

In step 402 of method 400, beginning from the proximal end of the coil, between six wires and 16 wires (e.g., ten wires) may be helically wound towards the distal end of the coil to form a proximal coil segment. The ten wires may be continuously wound so as to form the proximal coil segment as a single unitary structure. In some embodiments, the wires may be wound on a mandrel having a shape, dimensions, and configuration selected to produce a desired shape and size of the coil. In step 404 of method 400, upon forming the distal end of the proximal coil segment, a predetermined number (e.g., four) of the wires in the proximal coil segment may be cut or otherwise removed. In step 406 of method 400, the first transition segment of the coil may be formed by continuously winding the remaining wires towards the distal end of the coil. The first transition segment may include between four wires and nine wires (e.g., six wires). In some embodiments, the six wires may be wound along a corresponding section of the mandrel. In step 408 of method 400, upon forming the distal end of the first transition segment, a predetermined number (e.g., two) of the wires in the first transition segment may be cut or otherwise removed. In step 410 of method 400, the second transition segment of the coil may be formed by continuously winding the remaining wires towards the distal end of the coil. The second transition segment may include between three wires and eight wires (e.g., four wires). In some embodiments, the four wires may be wound along a corresponding section of the mandrel. In step 412 of method 400, upon forming the distal end of the second transition segment, a predetermined number (e.g., two) of the wires in the second transition segment may be cut or otherwise removed. In step 414 of method 400, the remaining wires may be continuously wound to form the distal coil segment. The distal coil segment may include between one wire and four wires (e.g., two wires). In an optional step 416 of method 400, after the wires are cut during the manufacturing method 400, the coil may be post-processed by cutting any excess wires and/or by covering exposed edges of the cut wires with a protective material, such as an adhesive, epoxy glue, heat shrink, polyether ether ketone (PEEK), and/or any other bonding material.

Advantageously, by cutting or otherwise removing wires from the coil in steps 404, 408, and 414, a gradual increase in flexibility may be formed from the proximal end of the coil to the distal end of the coil. In addition, forming the coil by gradually removing wires between coil segments may allow the entire coil to be formed as a single, unitary structure and obviate the need to incorporate rigid connections to connect separate segments together, thereby improving the flexibility of the coil.

Figure 5:
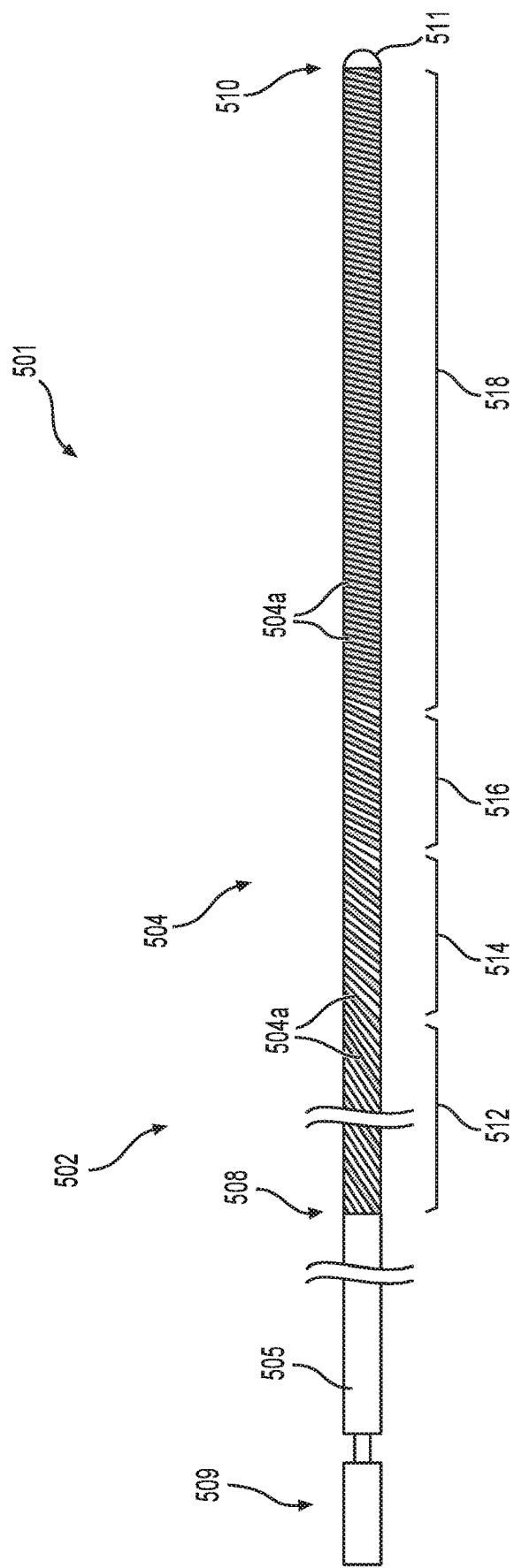
FIG. 5 illustrates another exemplary intraluminal device, consistent with various embodiments of the present disclosure.

FIG. 5 illustrates another exemplary intraluminal device 501 in a straightened configuration. Intraluminal device 501 may include an elongated sheath 502 that includes an elongated coil 504 and an elongated sheath 505 connected to the proximal end of coil 504. Intraluminal device 501 may also include a handle 509 connected to the proximal end of sheath 505. Coil 504 may be formed from a plurality of helically-wound wires and may have a similar configuration as elongated coil 104 of FIG. 1A: coil 504 may include a proximal coil segment 512, a first transition segment 514, a second transition segment 516, and a distal coil segment 518. In some embodiments, a dome cap 511 may be formed at the distal coil end 510. Proximal coil segment 512 may be formed from between five and 12 nitinol wires (e.g., eight nitinol wires) and between one wire and four wires (e.g., two wires 504a) that are formed of nitinol with radiopaque cores (e.g., 30% tantalum cores). These wires may be helically-wound to form the proximal coil segment 512, with a predetermined number (e.g., four) of the nitinol wires being cut at the distal end of proximal coil segment 512. The remaining wires (for example, between three and five nitinol wires and between one and four nitinol wires with radiopaque cores) may be helically wound to form the first transition segment 514, with at least one additional nitinol wire (for example, another two nitinol wires) being cut at the distal end of the first transition segment 514. The remaining wires (for example, between two and four nitinol wires and between one and four nitinol wires with radiopaque cores) may be helically wound to form the second transition segment 516, with the remaining nitinol wires without radiopaque cores being cut at the distal end of the second transition segment 516. The coil distal segment 518 may be formed from the nitinol wires with radiopaque cores. Accordingly, the entire axial length of the coil 504 may be radiopaque.

Figure 6B:
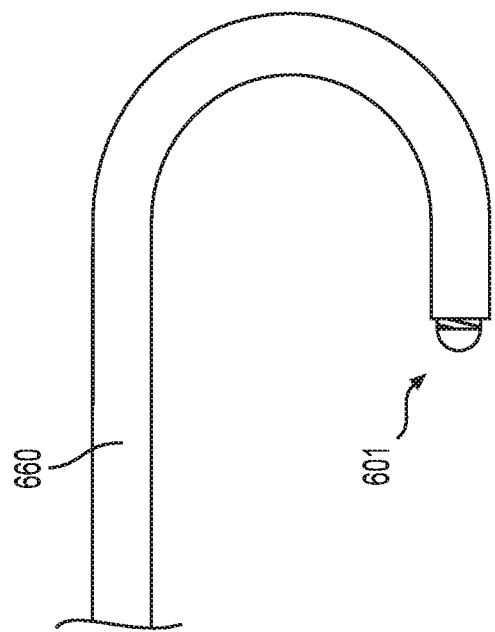
FIGS. 6A and 6B illustrate the advancement of a microcatheter over an exemplary intraluminal device, consistent with various embodiments of the present disclosure.
Figure 6A:
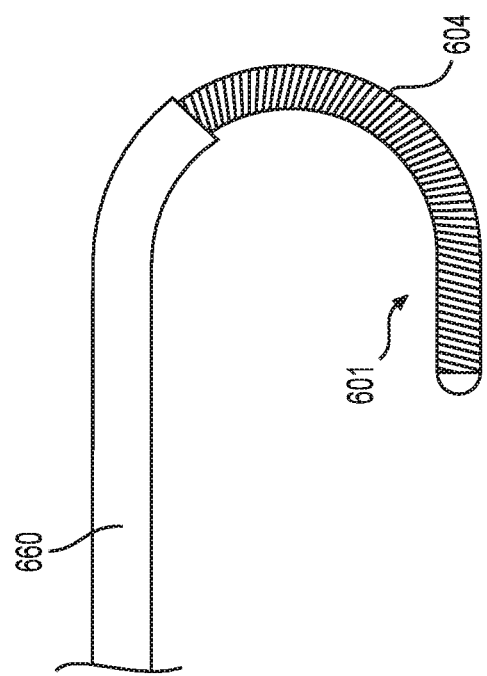

FIGS. 6A and 6B illustrate the advancement of a microcatheter 660 over an exemplary intraluminal device 601. Intraluminal device 601 may have the same or a similar configuration, for example, as intraluminal device 101 of FIG. 1A or intraluminal device 501 of FIG. 5. In some embodiments, intraluminal device 601 may include an elongated coil 604 and a looped core wire (not pictured) configured to bend the distal end of the coil 604 into a curved configuration. Intraluminal device 601 may provide internal support for the advancement of microcatheter 660 over the intraluminal device. As illustrated in FIG. 6B, intraluminal device 601 may be configured to shape the microcatheter 660, such that microcatheter 660 may assume a similar shape as the portion of intraluminal device 601 over which the microcatheter 660 has been advanced. In some embodiments, intraluminal device 601 may be navigated through the body until the distal end of intraluminal device 601 is placed at a desired anatomical location. For example, intraluminal device 601 may be placed at a location within the intracranial vessels. After placement of intraluminal device at the desired anatomical location, a second device (e.g., exemplary microcatheter 660) may be advanced over the intraluminal device 601 until the second device reaches the anatomical location. In some embodiments, the second device may be configured to perform a therapeutic and/or diagnostic process at the anatomical location.

FIG. 7A illustrates the distal portion of an exemplary intraluminal device 701 in a straightened configuration. FIG. 7B illustrates the distal portion of intraluminal device 701 in a curved configuration. Intraluminal device 701 may include an elongated coil 704 and a looped core wire 730 extending at least partially through coil 704. Coil 704 may include two or more segments with different degrees of flexibility, including a flexible distal coil segment 718 and a transition segment 716, which may be configured to be more rigid and less flexible than distal coil segment 718. Core wire 730 may include a distal end portion 750 with a first loop portion 736 that extends distally from a wider portion 735 of the core wire, a core wire bend 737 at which the core wire 730 may be bent or doubled back, and a second loop portion 738 extending between bend 737 and a distal tip 739 of the core wire. Core wire 730 may change from a distal axial direction (e.g., to the right in FIG. 7A) to a proximal axial direction (e.g., to the left in FIG. 7A) at core wire bend 737. In some embodiments, a portion of second loop portion 738 may be secured to coil 704 by a movement restrictor 746. In the embodiment illustrated in FIGS. 7A and 7B, the distal tip 739 may be placed in contact with movement restrictor 746. Alternatively, the second loop portion 738 may extend proximally beyond movement restrictor 746, so that the distal tip 739 may be situated proximally from movement restrictor 746. In some embodiments, core wire distal end portion 750 may have the same or a similar shape, size, and configuration as core wire distal end portion 250, as shown in FIG. 3A and described above in reference to FIG. 3A. The core wire bend 737 may be situated at or near the distal coil end 710.

In some embodiments, core wire bend 737 may be free from any direct bond or attachment to coil 704. When core wire 730 is subjected to an axially-directed force (e.g., a proximally-directed force), the force may cause the first loop portion 736 and second loop portion 738 to buckle into a curved configuration, such as the curved configuration of FIG. 7B. Due to the configuration of movement restrictor 746 as a hinge of core wire distal end portion 750, as discussed above in reference to FIGS. 3E-3G, first loop portion 736 and second loop portion 738 may buckle when an axially-directed force is applied to core wire 730. In some embodiments, the entire length of the coil 704 distal to movement restrictor 746 may be configured to bend due to the axial force application on core wire 730. As a result, some or all of distal coil segment 718 of intraluminal device 701 may be configured to bend due to axial force application on core wire 730.

Figure 8:
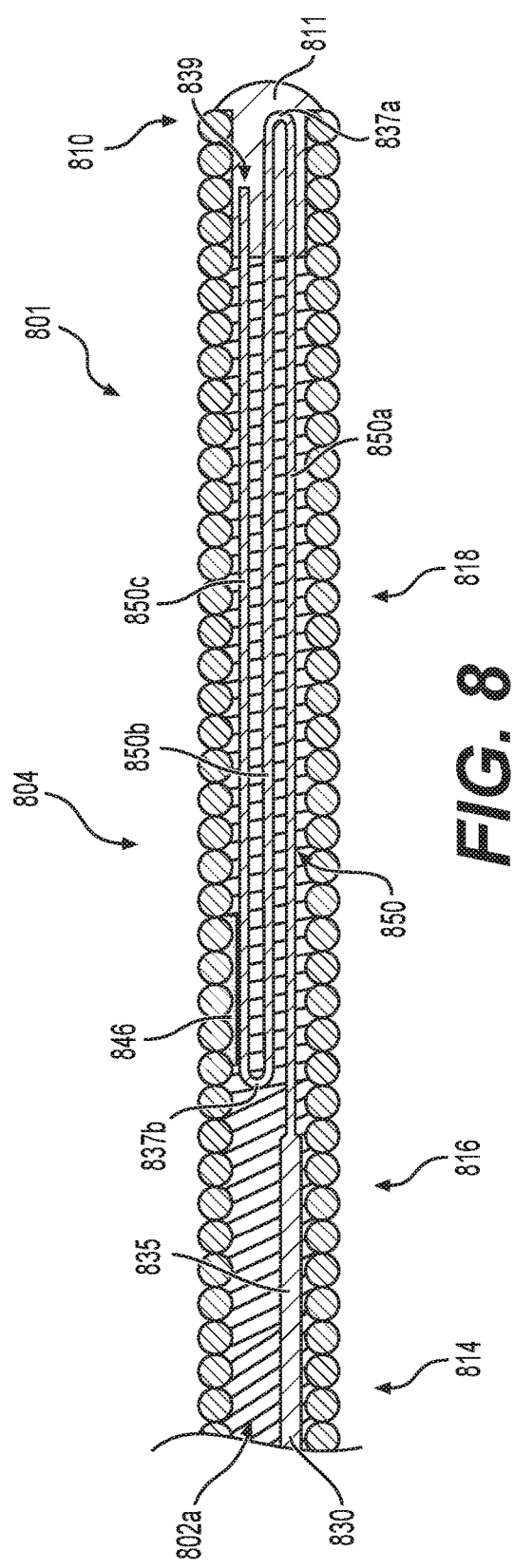
FIG. 8 illustrates the distal portion of another exemplary intraluminal device, consistent with various embodiments of the present disclosure.

FIG. 8 illustrates the distal portion of another exemplary intraluminal device 801 in a straightened configuration. Intraluminal device 801 may include an elongated coil 804 and a looped core wire 830 extending through an inner channel 802a of coil 804. Coil 804 may include two or more segments with different degrees of flexibility, including a first transition segment 814, a second transition segment 816 configured for greater flexibility than the first transition segment, and a distal coil segment 818 configured for greater flexibility than the second transition segment. Core wire 830 may include a distal end portion 850 having the same or a similar cross-sectional shape and size as core wire distal end portion 250, as depicted in FIG. 3A, or core wire distal end portion 750, as depicted in FIG. 7A.

In some embodiments, core wire distal end portion 850 may include a double turn in which, following the turn of core wire 830 at a first core wire bend 837a towards the proximal end of intraluminal device 801, core wire 830 may turn at a second core wire bend 837b back toward the distal end of intraluminal device 801. That is, core wire distal end portion 850 may include a first core wire bend 837a and a second core wire bend 837b at which core wire 830 may change from a proximal axial direction to a distal axial direction, or vice versa. A first loop portion 850a of the core wire may extend distally from a wider portion 835 of the core wire to first core wire bend 837a, which may be situated at or near distal coil end 810. A second loop portion 850b of the core wire may extend proximally from first core wire bend 837a to second core wire bend 837b, which may be situated proximally from first core wire bend 837a. A third loop portion 850c of the core wire may extend distally from second core wire bend 837b to distal tip 839 of the core wire. In some embodiments, distal tip 839 may be situated at the same axial position as first core wire bend 837a. Alternatively, distal tip 839 may be situated proximally or distally from first core wire bend 837a. In some embodiments, one or both of first loop portion 850a or third loop portion 850c may have the same or a similar axial length as first loop portion 236 of FIG. 2. Additionally, or alternatively, second loop portion 850b may have the same or a similar axial length as second loop portion 238 of FIG. 2.

In some embodiments, intraluminal device 801 may include a movement restrictor 846, which may be situated at or near second core wire bend 837b. Although FIG. 8 depicts movement restrictor 846 situated along one side of inner channel 802a, movement restrictor 846 may alternatively be situated along two opposite sides of inner channel 802a, similar to the configuration of movement restrictor 346 depicted in FIG. 3D. Movement restrictor 846 may contact at least a portion of third loop portion 850c, thus bonding core wire distal end portion 850 to coil 804. Additionally, or alternatively, intraluminal device 801 may include a dome cap 811 at the coil distal end 810. Dome cap 811 may be constructed of epoxy and may be rounded to prevent injury to tissue. As shown in FIG. 8, first core wire bend 837a and core wire distal tip 839 may be encompassed within dome cap 811. Dome cap 811 may be formed, in part, by filling inner channel 802a with epoxy near coil distal end 810, such that the epoxy covers first core wire bend 837a and core wire distal tip 839 and contacts the walls of the inner channel 802a. Accordingly, dome cap 811 may bond first core wire bend 837a and core wire distal tip 839 to each other and to coil distal end 810.

When core wire 830 is subjected to an axially-directed force, the force may cause loop sections 850a, 850b, and 850c to buckle, forcing the distal portion of intraluminal device 801 to bend radially into a curved configuration. Due to the configuration of movement restrictor 846 as a hinge of core wire distal end portion 850, as discussed above in reference to FIGS. 3E-3G, loop sections 850a, 850b, and 850c may buckle when an axially-directed force is applied to core wire 830. In some embodiments, some or all of the distal coil segment 818 may be configured to bend due to axial force application on core wire 830.

Figure 9:
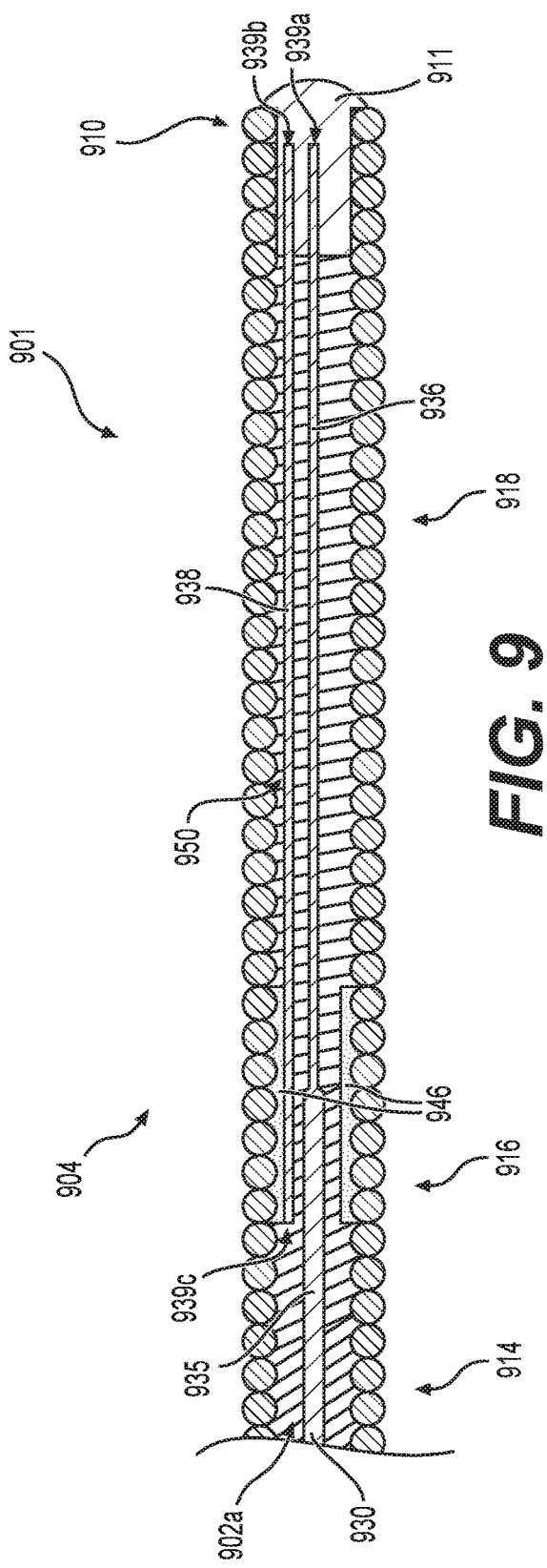
FIG. 9 illustrates the distal portion of a further exemplary intraluminal device, consistent with various embodiments of the present disclosure.

FIG. 9 illustrates the distal portion of a further exemplary intraluminal device 901 in a straightened configuration. Intraluminal device 901 may include an elongated coil 904 and a looped core wire 930 extending through an inner channel 902a of coil 904. Coil 904 may include two or more segments with different degrees of flexibility, including a first transition segment 914, a second transition segment 916 configured for greater flexibility than the first transition segment, and a distal coil segment 918 configured for greater flexibility than the second transition segment. In some embodiments, a movement restrictor 946 may be provided within coil 904 as an anti-rotation mechanism; movement restrictor 946 may include a polymer (e.g., PEEK), an adhesive, a weld, and/or any other suitable material and may have the same or a similar configuration as movement restrictor 346 of FIG. 3A or movement restrictor 746 of FIG. 7A. Core wire 930 may include a distal end portion 950 having the same or a similar cross-sectional shape and size as core wire distal end portion 250 of FIG. 3A, core wire distal end portion 750 of FIG. 7A, or core wire distal end portion 850 of FIG. 8.

In some embodiments, core wire distal end portion 950 may include two disjointed loop portions 936 and 938. First loop portion 936 may extend distally from a wider portion 935 of the core wire to a first distal tip 939a, which may be situated at or near distal coil end 910. Accordingly, first loop portion 936 may form the distal-most section of the part of the core wire that extends to the proximal end of intraluminal device 901. Second loop portion 938 may have a first end that forms a second distal tip 939b and may extend proximally from second distal tip 939b to a proximal tip 939c. In some embodiments, first distal tip 939a may be situated at the same axial position as second distal tip 939b. Alternatively, first distal tip 939a may be situated proximally or distally from second distal tip 939b. In some embodiments, at least a portion of second loop portion 938 may be secured to coil 904 by the movement restrictor 946 (which may include, for example, a bonding polymer such as PEEK). In the embodiment illustrated in FIG. 9, proximal tip 939c may be placed in contact with the movement restrictor 946. Alternatively, second loop portion 938 may extend proximally beyond movement restrictor 946, so that proximal tip 939c may be situated proximally from movement restrictor 946.

In some embodiments, intraluminal device 901 may include a dome cap 911 at coil distal end 910. Dome cap 911 may be constructed of epoxy and may be rounded to prevent injury to tissue. As shown in FIG. 9, first distal tip 939a and second distal tip 939b may be encompassed within dome cap 911. Dome cap 911 may be formed, in part, by filling inner channel 902a with epoxy near coil distal end 910, such that the epoxy covers first distal tip 939a and second distal tip 939b and contacts the walls of the inner channel 902a. Accordingly, dome cap 911 may bond first distal tip 939a and second distal tip 939b to each other and to coil distal end 910.

When core wire 930 is subjected to an axially-directed force, the force may cause first loop portion 936 and second loop portion 938 to buckle, forcing the distal portion of intraluminal device 901 to bend radially into a curved configuration. Due to the configuration of movement restrictor 946 as a hinge of core wire distal end portion 950, as discussed above in reference to FIGS. 3E-3G, first loop portion 936 and second loop portion 938 may buckle when an axially-directed force is applied to core wire 930. In some embodiments, some or all of the distal coil segment 918 may be configured to bend due to axial force application on core wire 930.

Figure 10:
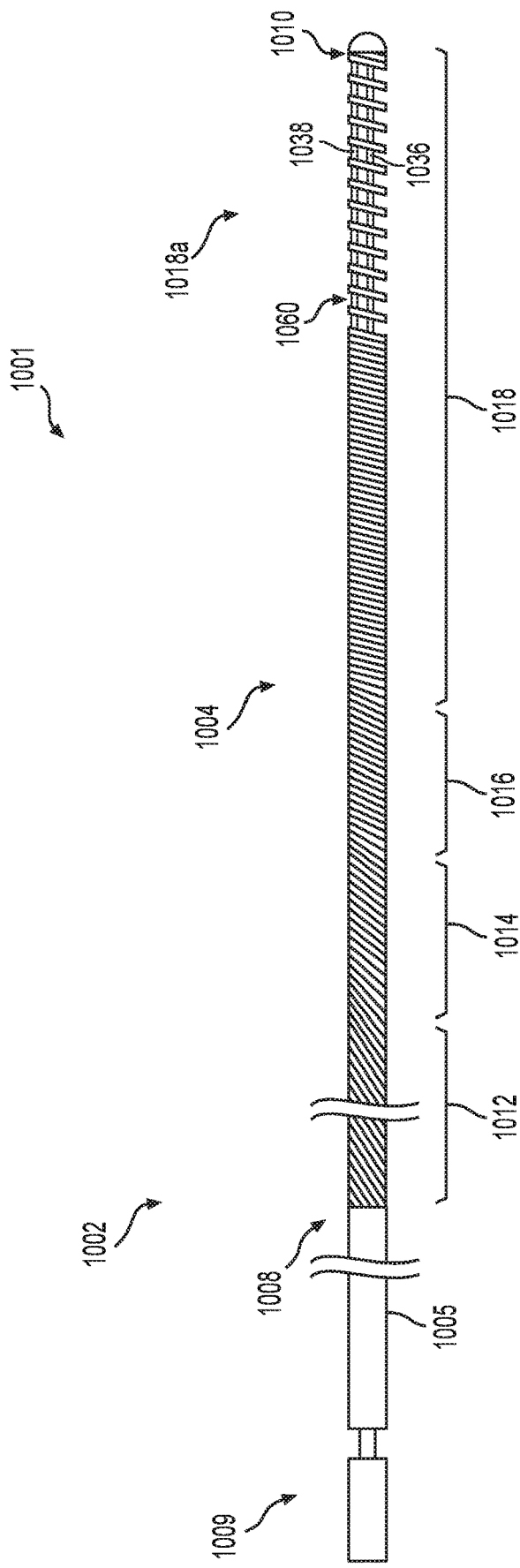
FIG. 10 illustrates another exemplary intraluminal device, consistent with various embodiments of the present disclosure.

FIG. 10 illustrates an exemplary intraluminal device 1001, according to various embodiments of the present disclosure. Intraluminal device 1001 may include an elongated sheath 1002 having an elongated shaft 1005 and an elongated coil 1004 connected to the distal end of the elongated shaft 1005, coil 1004 extending between a coil proximal end 1008 and a coil distal end 1010. Intraluminal device 1001 may also include a handle 1009 connected to the proximal end of elongated shaft 1005. Handle 1009 may be connected to a looped wire core extending through elongated shaft 1005 and coil 1004 and configured to control movement (e.g., bending and straightening) of at least a portion of coil 1004. The looped core wire of intraluminal device 1001 may include a first loop portion 1036, a bend (not shown in FIG. 10) situated at or near the distal coil end 1010, and a second loop portion 1038. Elongated coil 1004 may be formed from a plurality of helically-wound wires, at least some of which extend from coil proximal end 1008 to coil distal end 1010. Elongated coil 1004 may include a proximal coil segment 1012, a first transition segment 1014, a second transition segment 1016, and a distal coil segment 1018.

In some embodiments, spaces 1060 may be formed between the wound wires (i.e., the windings) of coil 1004 in one or more of the coil segments. For example, as shown in FIG. 10, spaces 1060 may be formed between each wire in a distal portion 1018a of distal coil segment 1018, which may further increase the flexibility of distal portion 1018a. In some embodiments, spaces 1060 may be provided along the entire axial length of distal coil segment 1018. Additionally, or alternatively, similar spaces may be provided between the windings in second transition segment 1016, first transition segment 1014, and/or proximal coil segment 1012. In some embodiments, at least a portion of coil 1014 (e.g., proximal coil segment 1012) may lack spaces 1060 between the windings therein to ensure an increase in coil flexibility towards the distal end of coil 1004.

In some embodiments, spaces 1060 between the windings of coil 1004 may be evenly spaced along the longitudinal axis of coil 1004 and may be approximately equal in axial length. In some alternative embodiments, the axial lengths of spaces 1060 may vary along the longitudinal axis of coil 1004, so as to render certain portions of coil 1004 more flexible than other portions of coil 1004. In some embodiments, spaces 1060 may be formed during the process of winding the plurality of wires to form the elongated coil 1004 by adding gaps between the wires at a predetermined frequency. In some alternative embodiments, spaces 1060 may be formed by removing one or more wires from the desired portion(s) of the elongated coil 1004, e.g., by cutting. Optionally, the wires in proximity to spaces 1060 may be reinforced to maintain spaces 1060 and to hold the wires at their intended coil angle(s), for example, by heat treating the wires to reinforce the wires at their intended coil angle(s). Advantageously, the formation of spaces 1060 within the elongated coil 1004 may increase the flexibility of the corresponding section(s) of the coil. For example, spaces 1060 may be formed within a portion or within all of the distal coil segment 1018 to form a soft, atraumatic distal tip of intraluminal device 1001.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An intraluminal device, comprising:
    a flexible, elongated sheath having a proximal section and a distal section, the distal section of the sheath terminating in a distal end of the sheath, wherein the distal section of the sheath has a distal bending segment and a proximal support segment situated proximally from the distal bending segment, the distal bending segment being configured for greater flexibility than the proximal support segment;
    an elongated core wire extending between a proximal tip of the core wire and a distal tip of the core wire, the core wire being situated at least partially within the sheath, wherein the core wire comprises a distal end portion doubled back in a loop within the sheath such that at least a portion of the core wire is situated proximally from the loop of the core wire, wherein the loop of the core wire includes a double turn, such that following a turn of the core wire toward a proximal end of the sheath, the core wire turns back toward the distal end of the sheath; and
    a movement restrictor situated at least partially within the sheath, the movement restrictor being configured to limit axial movement of the distal tip of the core wire in at least one axial direction and to permit the loop of the core wire to buckle, resulting in a bend in the distal section of the sheath, when an axial force is exerted on the core wire.

2. The intraluminal device of claim 1, wherein the movement restrictor comprises:
    a bond between the core wire and an inner wall of the sheath, the bond situated proximally from the distal tip of the core wire.

3. The intraluminal device of claim 2, wherein the bond is formed by at least one of an adhesive or a weld.

4. The intraluminal device of claim 1, wherein the movement restrictor comprises:
an insert situated within an inner channel of the sheath, the insert comprising at least one of an obstruction or a ring connected to a wall of the inner channel of the sheath.

5. The intraluminal device of claim 1, wherein at least a portion of the sheath comprises:
a coil including one or more wires wound to form a plurality of windings, at least some of the windings of the coil forming the distal section of the sheath.

6. The intraluminal device of claim 5, wherein at least some of the windings forming the distal section of the sheath are configured to have spaces therebetween.

7. The intraluminal device of claim 6,
wherein at least a portion of the proximal section of the sheath is formed of windings of the coil, and
wherein at least some of the windings forming the proximal section of the sheath lack spaces therebetween.

8. The intraluminal device of claim 1,
wherein the distal section of the sheath includes a coil, and
wherein at least a portion of the proximal section of the sheath is formed of a construct other than a coil.

9. The intraluminal device of claim 1, wherein a portion of the core wire in the distal section of the sheath is configured such that repeated exertions of force on the core wire result in repeatably consistent directional flexing of the core wire.

10. The intraluminal device of claim 9, wherein the distal end portion of the core wire has a non-circular cross-section that is configured to enable preferential bending of the core wire.

11. The intraluminal device of claim 1, wherein the loop of the core wire is configured to form a gap between the loop of the core wire and an inner wall of the sheath, the gap being sized such that a portion of the loop of the core wire is configured to distort within the gap when the core wire is subject to an applied force.

12. The intraluminal device of claim 11, wherein the distortion of the core wire within the gap includes a buckling of the core wire within the gap.

13. The intraluminal device of claim 1, wherein the loop of the core wire is configured such that when the core wire is moved distally, at least a portion of the loop does not move in a distal direction relative to the distal section of the sheath.

14. The intraluminal device of claim 1, further comprising:
a widening of the core wire situated proximally of the distal end portion.

15. The intraluminal device of 1, wherein the sheath and the core wire are biased in a straightened configuration and are configured such that an axial pulling force on the core wire causes bending of the distal bending segment of the sheath.

16. The intraluminal device of claim 1, wherein the sheath is configured to traverse the vasculature within a human brain.

17. The intraluminal device of claim 1,
wherein the movement restrictor is a step formed within the inner channel of the sheath, and
wherein an edge of the distal end portion of the core wire is positioned against the step.

18. The intraluminal device of claim 17, wherein the core wire is positioned against the step at a location proximally spaced from the distal tip of the core wire.

19. The intraluminal device of claim 1, wherein the core wire extends continuously through the loop of the core wire.

20. The intraluminal device of claim 1, wherein the movement restrictor is a narrowing of an inner channel of the sheath.

21. The intraluminal device of claim 1, wherein the loop of the core wire is disjointed into two segments at a bend thereof and the disjointed segments of the core wire are bonded together.

* * * * *